US012710423B2

(12) United States Patent
Van Den Born et al.

(10) Patent No.: US 12,710,423 B2

(45) Date of Patent: Aug. 18, 2026

(54) AFRICAN SWINE FEVER DIVA IMMUNOASSAY

(71) Applicant: INTERVET INC., Madison, NJ (US)

(72) Inventors: Erwin Van Den Born, Wageningen (NL); Urs Peter Bruderer, Kleve (DE)

(73) Assignee: Intervet Inc., Rahway, NJ (US)

( * ) Notice: Subject to any disclaimer, the term of this patent is extended or adjusted under 35 U.S.C. 154(b) by 553 days.

(21) Appl. No.: 18/257,896

(22) PCT Filed: Dec. 23, 2021

(86) PCT No.: PCT/EP2021/087447

§ 371 (c)(1),
(2) Date: Jun. 16, 2023

(87) PCT Pub. No.: WO2022/136624

PCT Pub. Date: Jun. 30, 2022

(65) Prior Publication Data

US 2024/0053340 A1 Feb. 15, 2024

(30) Foreign Application Priority Data

Dec. 24, 2020 (EP) .................................... 20217271

(51) Int. Cl.
*G01N 33/569* (2006.01)

(52) U.S. Cl.
CPC ... *G01N 33/56983* (2013.01); *G01N 2333/01* (2013.01); *G01N 2469/20* (2013.01)

(58) Field of Classification Search
CPC .................................................... G01N 33/569
See application file for complete search history.

(56) References Cited

U.S. PATENT DOCUMENTS

| | | | | |
|---|---|---|---|---|
| 9,808,520 | B1 | 11/2017 | Borca et al. | |
| 2012/0315295 | A1* | 12/2012 | Rieder | C12Q 1/701 435/235.1 |
| 2015/0165018 | A1 | 6/2015 | Rodriguez et al. | |
| 2020/0306360 | A1 | 10/2020 | Nikolin et al. | |
| 2025/0127881 | A1* | 4/2025 | Sahin | G01N 33/56983 |

FOREIGN PATENT DOCUMENTS

| | | | |
|---|---|---|---|
| CN | 110759973 | A | 2/2020 |
| CN | 111518174 | A | 8/2020 |
| CN | 111961120 | A | 11/2020 |
| RU | 2654586 | C2 | 5/2018 |
| RU | 2019105532 | A | 8/2020 |
| WO | 2002085932 | A2 | 10/2002 |
| WO | 2012143709 | A1 | 10/2012 |
| WO | WO 2020102370 | A1 | 5/2020 |

OTHER PUBLICATIONS

Arias et al. (Vaccines, 2017, p. 1-20 in IDS on Dec. 23, 2024).*
Arias et al., 2017, "Approaches and Perspectives for Development of African Swine Fever Virus Vaccines," Vaccines (Basel), 5(4):35 (20 pages).
Monteagudo et al., 2017, "BA71ΔCD2: a New Recombinant Live Attenuated African Swine Fever Virus with Cross-Protective Capabilities," J. Virol., 91(21):e01058-17 (17 pages).
Rock, 2017, "Challenges for African swine fever vaccine development—" . . . perhaps the end of the beginning."" Vet. Microbiol., 206:52-58 (Epub 2016).
Sanchez et al., 2019, "Development of vaccines against African swine fever virus," Virus Res., 265:150-155.
Wang et al., 2020, "Multifaceted Immune Responses to African Swine Fever Virus: Implications for Vaccine Development," Vet. Microbiol., 249:108832 (10 pages).

* cited by examiner

*Primary Examiner* — Agnieszka Boesen
(74) *Attorney, Agent, or Firm* — Susanna C. Benn

(57) ABSTRACT

The invention relates to a diagnostic use of an African Swine Fever Vims CD2v protein, a method, a device, and a kit for the detection of the presence of ASFV antibodies in a test sample, in particular the use thereof in a DIVA immunoassay.

14 Claims, 11 Drawing Sheets

Figure 1:
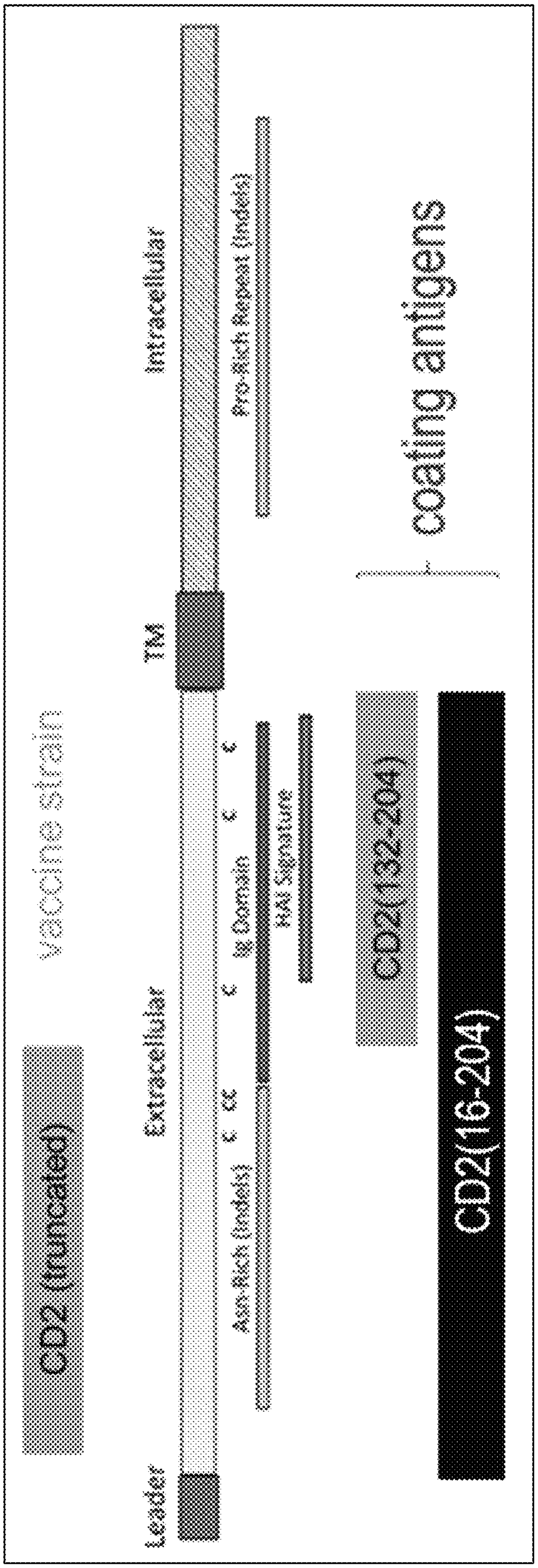

Specification includes a Sequence Listing.

Figure 2 - continued

```
                       321 .         .         :         .         .         .         .         4 400
 1 Rhodesia                PPKPCPPPKPCPP------------------------------PKPCPSSESCSPPESYSLPKPLPNI--PLLPNIPPLS
 2 LV17/WB/Rie1            --------------------------------------------------------------------------------
 3 VN/Pig/HN/19            PPKPCPPPKPCPS------------------------------------------AESYSPPKPLPSI--PLLPNIPPLS
 4 Pol19_53050_C195        PPKPCPPPKPCPS------------------------------------------AESYSPPKPLPSI--PLLPNIPPLS
 5 wbBS01                  PPKPCPPPKPCPS------------------------------------------AESYSPPKPLPSI--PLLPNIPPLS
 6 Georgia2007             PPKPCPPPKPCPS------------------------------------------AESYSPPKPLPSI--PLLPNIPPLS
 7 Volgograd_2012          PPKPCPPPKPCPS------------------------------------------AESYSPPKPLPSI--PLLPNIPPLS
 8 VNUA/HY                 PPKPCPPPKPCPS------------------------------------------AESYSPPKPLPSI--PLLPNIPPLS
 9 NHV                     THFPY-----------------------------------------------------LNHARHLNHVLHPSHARHPNLS
10 OURT                    THFPY-----------------------------------------------------LNHARHLNHVLHPSHARHPNLS
11 Liv13/33                PPKPCPPPKPCPS------------------------------PKPCPPPKPCPSPESYSPPKPLPNI--PLLPNIPPLS
12 Lisbon60                PPKPCPPPKPCPTPKPCSPPKPCRPPKPCPPPKPCPPPKPCPPPKPCPPSKPCPSPESYSPPKPLPSI--PLLSNIPPLS
13 47/Ss/2008              PPKPCPPPKPCPPPKPCSPPKPCRPPKPCPPPKPCPPPKPCPPPKPCPPPKPCPSPESYSPPKPLPSI--PLLPNIPPLS
14 BA71                    PPKPCPPPKPCPPPKPCSPPKPCRPPKPCPPPKPCPPPKPCPPPKPCPPSKPCPSPESYSPPKPLPSI--PLLPNIPPLS
15 P-60                    PPKPCPPPKPCPPPKPCSPPKPCRPPKPCPPPKPCPPPKPCPPPKPCPPSKPCPSPESYSPPKPLPSI--PLLPNIPPLS

                       401         . ] 413
 1 Rhodesia                TQNISLIHVDRII
 2 LV17/WB/Rie1            -------------
 3 VN/Pig/HN/19            TQNISLIPLDRIF
 4 Pol19_53050_C195        TQNISLIHVDRII
 5 wbBS01                  TQNISLIHVDRII
 6 Georgia2007             TQNISLIHVDRII
 7 Volgograd_2012          TQNISLIHVDRII
 8 VNUA/HY                 TQNISLIHVDRII
 9 NHV                     ST-----------
10 OURT                    ST-----------
11 Liv13/33                TQNISLIHVDRII
12 Lisbon60                TQNISLIHVDRII
13 47/Ss/2008              TQNISLIHVDRII
14 BA71                    TQNISLIHVDRII
15 P-60                    TQNISLIHVDRII
```

A
PBS+3% Tween + 0.1 M MgCl2
B
PBS+3% Tween +0.33 M MgCl2
C
PBS+3%Tween+ 1 M MgCl2
D
LSHD
Relative OD450
Realtive OD450
2,5000
2,0000
1,5000
1,0000
0,5000
0,0000
1:100
1:300
1:900
1:2700
1:8100
1:24300
1:72900
Neg
C+113 (I/I/II)
C-67 (neg)
S3 (II, vaccine)

A
PBS+3% Tween20
Relative OD450
2,5
2
1,5
1
0,5
0
1:100
1:300
1:900
1:2700
1:8100
1:24300
1:72900
Neg
C+113 (I/I/II)
C-67 (neg)
S3 (II, vaccine)
B
PBS+3%Tween20+ 0.1 M MgCl2
Relative OD450
2,5
2
1,5
1
0,5
0
1:100
1:300
1:900
1:2700
1:8100
1:24300
1:72900
Neg
C+113 (I/I/II)
C-67 (neg)
S3 (II, vaccine)
C
3%Tween20+0.1 M MgCl2
Relative OD450
2,5
2
1,5
1
0,5
0
1:100
1:300
1:900
1:2700
1:8100
1:24300
1:72900
Neg
C+113 (I/I/II)
C-67 (neg)
S3 (II, vaccine)
D
LSHD
Relative OD450
2,5
2
1,5
1
0,5
0
1:100
1:300
1:900
1:2700
1:8100
1:24300
1:72900
Neg
C+113 (I/I/II)
C-67 (neg)
S3 (II, vaccine)

SEQUENCE LISTING

<160> NUMBER OF SEQ ID NOS: 25

<210> SEQ ID NO 1
<211> LENGTH: 360
<212> TYPE: PRT
<213> ORGANISM: African swine fever virus

<400> SEQUENCE: 1

```
Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile
        355                 360
```

-continued

<210> SEQ ID NO 2
<211> LENGTH: 189
<212> TYPE: PRT
<213> ORGANISM: African swine fever virus

<400> SEQUENCE: 2

Ile Asp Tyr Trp Val Ser Phe Asn Lys Thr Ile Ile Leu Asp Ser Asn
1               5                   10                  15

Ile Thr Asn Asp Asn Asn Asp Ile Asn Gly Val Ser Trp Asn Phe Phe
            20                  25                  30

Asn Asn Ser Phe Asn Thr Leu Ala Thr Cys Gly Lys Ala Gly Asn Phe
        35                  40                  45

Cys Glu Cys Ser Asn Tyr Ser Thr Ser Ile Tyr Asn Ile Thr Asn Asn
    50                  55                  60

Cys Ser Leu Thr Ile Phe Pro His Asn Asp Val Phe Asp Thr Thr Tyr
65                  70                  75                  80

Gln Val Val Trp Asn Gln Ile Ile Asn Tyr Thr Ile Lys Leu Leu Thr
                85                  90                  95

Pro Ala Thr Pro Pro Asn Ile Thr Tyr Asn Cys Thr Asn Phe Leu Ile
            100                 105                 110

Thr Cys Lys Lys Asn Asn Gly Thr Asn Thr Asn Ile Tyr Leu Asn Ile
        115                 120                 125

Asn Asp Thr Phe Val Lys Tyr Thr Asn Glu Ser Ile Leu Glu Tyr Asn
    130                 135                 140

Trp Asn Asn Ser Asn Ile Asn Asn Phe Thr Ala Thr Cys Ile Ile Asn
145                 150                 155                 160

Asn Thr Ile Ser Thr Ser Asn Glu Thr Thr Leu Ile Asn Cys Thr Tyr
                165                 170                 175

Leu Thr Leu Ser Ser Asn Tyr Phe Tyr Thr Phe Phe Lys
            180                 185

<210> SEQ ID NO 3
<211> LENGTH: 73
<212> TYPE: PRT
<213> ORGANISM: African swine fever virus

<400> SEQUENCE: 3

Asn Asn Gly Thr Asn Thr Asn Ile Tyr Leu Asn Ile Asn Asp Thr Phe
1               5                   10                  15

Val Lys Tyr Thr Asn Glu Ser Ile Leu Glu Tyr Asn Trp Asn Asn Ser
            20                  25                  30

Asn Ile Asn Asn Phe Thr Ala Thr Cys Ile Ile Asn Asn Thr Ile Ser
        35                  40                  45

Thr Ser Asn Glu Thr Thr Leu Ile Asn Cys Thr Tyr Leu Thr Leu Ser
    50                  55                  60

Ser Asn Tyr Phe Tyr Thr Phe Phe Lys
65                  70

<210> SEQ ID NO 4
<211> LENGTH: 10
<212> TYPE: PRT
<213> ORGANISM: Artificial Sequence
<220> FEATURE:
<223> OTHER INFORMATION: c-myc domain

<400> SEQUENCE: 4

Glu Gln Lys Leu Ile Ser Glu Glu Asp Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: heamagglutinin tag

<400> SEQUENCE: 5

```
Tyr Pro Tyr Asp Val Pro Asp Tyr Ala
1               5
```

<210> SEQ ID NO 6
<211> LENGTH: 20
<212> TYPE: PRT
<213> ORGANISM: Artificial Sequence
<220> FEATURE:
<223> OTHER INFORMATION: GP64 signal peptide

<400> SEQUENCE: 6

```
Met Val Ser Ala Ile Val Leu Tyr Val Leu Leu Ala Ala Ala Ala His
1               5                   10                  15

Ser Ala Phe Ala
            20
```

<210> SEQ ID NO 7
<211> LENGTH: 4
<212> TYPE: PRT
<213> ORGANISM: Artificial Sequence
<220> FEATURE:
<223> OTHER INFORMATION: Linker

<400> SEQUENCE: 7

```
Gly Gly Gly Ser
1
```

<210> SEQ ID NO 8
<211> LENGTH: 375
<212> TYPE: PRT
<213> ORGANISM: African swine fever virus

<400> SEQUENCE: 8

```
Met Ile Ile Ile Leu Ile Phe Leu Ile Ile Ser Asn Ile Val Leu Ser
1               5                   10                  15

Ile Asp Tyr Trp Val Ser Phe Asn Lys Thr Ile Ile Leu Asp Ser Asn
            20                  25                  30

Ile Thr Asn Asp Asn Asn Asp Ile Asn Gly Val Ser Trp Asn Phe Phe
        35                  40                  45

Asn Asn Ser Phe Asn Thr Leu Ala Thr Cys Gly Lys Ala Gly Asn Phe
    50                  55                  60

Cys Glu Cys Ser Asn Tyr Ser Thr Ser Ile Tyr Asn Ile Thr Asn Asn
65                  70                  75                  80

Cys Ser Leu Thr Ile Phe Pro His Asn Asp Val Phe Asp Thr Thr Tyr
                85                  90                  95

Gln Val Val Trp Asn Gln Ile Ile Asn Tyr Thr Ile Lys Leu Leu Thr
            100                 105                 110

Pro Val Thr Pro Pro Asn Ile Thr Tyr Asn Cys Thr Asn Phe Leu Ile
        115                 120                 125

Thr Cys Lys Lys Asn Asn Gly Thr Asn Thr Asn Ile Tyr Leu Asn Ile
    130                 135                 140

Asn Asp Thr Asn Val Lys Tyr Thr Asn Glu Ser Ile Leu Glu Tyr Asn
```

-continued

```
145                 150                 155                 160

Trp Asn Asn Ser Asn Phe Asn Asn Phe Thr Ala Thr Cys Ile Ile Asn
                165                 170                 175

Asn Thr Ile Asn Ser Ser Asn Asp Thr Gln Thr Ile Asp Cys Ile Asn
            180                 185                 190

Thr Leu Leu Ser Ser Tyr Leu Asp Phe Phe Gln Val Ala Ser Tyr Met
        195                 200                 205

Phe Tyr Met Ile Ile Phe Ile Ala Thr Gly Ile Ile Ala Ser Ile Phe
    210                 215                 220

Ile Ser Ile Ile Thr Phe Leu Ser Leu Arg Lys Arg Lys Lys His Val
225                 230                 235                 240

Glu Glu Ile Glu Ser Pro Ser Pro Ser Glu Ser Asn Glu Glu Glu Gln
                245                 250                 255

Cys Gln His Asp Asp Thr Thr Ser Ile His Glu Pro Ser Pro Arg Glu
            260                 265                 270

Pro Leu Leu Pro Lys Pro Tyr Ser Arg Tyr Gln Tyr Asn Thr Pro Ile
        275                 280                 285

Tyr Tyr Met Arg Pro Leu Thr Gln Pro Leu Asn Pro Ser Pro Leu Pro
    290                 295                 300

Lys Leu Cys Pro Pro Pro Lys Pro Cys Pro Pro Pro Lys Pro Cys Pro
305                 310                 315                 320

Pro Pro Lys Pro Cys Pro Pro Pro Lys Pro Cys Pro Ser Ser Glu Ser
                325                 330                 335

Cys Ser Pro Pro Glu Ser Tyr Ser Leu Pro Lys Pro Leu Pro Asn Ile
            340                 345                 350

Pro Leu Leu Pro Asn Ile Pro Pro Leu Ser Thr Gln Asn Ile Ser Leu
        355                 360                 365

Ile His Val Asp Arg Ile Ile
    370                 375


<210> SEQ ID NO 9
<211> LENGTH: 140
<212> TYPE: PRT
<213> ORGANISM: African swine fever virus

<400> SEQUENCE: 9

Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Ile Met Glu Gln Thr Leu Ile Tyr Ile
    130                 135                 140
```

<210> SEQ ID NO 10
<211> LENGTH: 360
<212> TYPE: PRT
<213> ORGANISM: African swine fever virus

<400> SEQUENCE: 10

Met Ile Ile Ile Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile Pro Leu Asp Arg Ile Phe
        355                 360

<210> SEQ ID NO 11

<211> LENGTH: 360
<212> TYPE: PRT
<213> ORGANISM: African swine fever virus

<400> SEQUENCE: 11

```
Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Leu Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile
        355                 360
```

<210> SEQ ID NO 12
<211> LENGTH: 360
<212> TYPE: PRT

<213> ORGANISM: African swine fever virus

<400> SEQUENCE: 12

```
Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile
        355                 360
```

<210> SEQ ID NO 13
<211> LENGTH: 360
<212> TYPE: PRT
<213> ORGANISM: African swine fever virus -continued

<400> SEQUENCE: 13

```
Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile
        355                 360
```

<210> SEQ ID NO 14
<211> LENGTH: 360
<212> TYPE: PRT
<213> ORGANISM: African swine fever virus

<400> SEQUENCE: 14

-continued

```
Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile
        355                 360


<210> SEQ ID NO 15
<211> LENGTH: 360
<212> TYPE: PRT
<213> ORGANISM: African swine fever virus

<400> SEQUENCE: 15

Met Ile Ile Leu Ile Phe Leu Ile Phe Ser Asn Ile Val Leu Ser Ile
1               5                   10                  15
```

-continued

```
Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile
        355                 360


<210> SEQ ID NO 16
<211> LENGTH: 304
<212> TYPE: PRT
<213> ORGANISM: African swine fever virus

<400> SEQUENCE: 16

Met Glu Tyr Phe Lys Ser Asn Cys Ile Leu Asn Asn Ile Phe Thr Ile
1               5                   10                  15

Asn Asp Thr Tyr Gly Gly Leu Phe Trp Asn Thr Tyr Tyr Asp Asn Asn
```

-continued

```
            20                  25                  30

Arg Ser Asn Phe Thr Tyr Cys Gly Ile Ala Gly Asn Tyr Cys Ser Cys
        35                  40                  45

Cys Gly His Asn Ile Ser Leu Tyr Asn Thr Thr Asn Asn Cys Ser Leu
    50                  55                  60

Ile Ile Phe Pro Asn Asn Thr Glu Ile Phe Asn Arg Thr Tyr Glu Leu
65                  70                  75                  80

Val Tyr Leu Asp Lys Lys Ile Asn Tyr Thr Val Lys Leu Leu Lys Ser
                85                  90                  95

Val Asp Ser Pro Thr Ile Thr Tyr Asn Cys Thr Asn Ser Leu Ile Thr
            100                 105                 110

Cys Lys Asn Asn Asn Gly Thr Asn Val Asn Ile Tyr Leu Ile Ile Asn
        115                 120                 125

Asn Thr Ile Val Asn Asp Thr Asn Gly Asp Ile Leu Asn Tyr Tyr Trp
    130                 135                 140

Asn Gly Asn Asn Asn Phe Thr Ala Thr Cys Met Ile Asn Asn Thr Ile
145                 150                 155                 160

Ser Ser Leu Asn Glu Thr Glu Asn Ile Asn Cys Thr Asn Pro Ile Leu
                165                 170                 175

Lys Tyr Gln Asn Tyr Leu Ser Thr Leu Phe Tyr Ile Ile Ile Phe Ile
            180                 185                 190

Val Ser Gly Leu Ile Ile Gly Ile Phe Ile Ser Ile Ile Ser Val Leu
        195                 200                 205

Ser Ile Arg Arg Lys Arg Lys Lys His Val Glu Glu Ile Glu Ser Pro
    210                 215                 220

Pro Pro Ser Glu Ser Asn Glu Glu Asp Ile Ser His Asp Asp Thr Thr
225                 230                 235                 240

Ser Ile His Glu Pro Ser Pro Glu Asn His Tyr Phe Leu Ser Leu Thr
                245                 250                 255

Val Val Ile Ser Ile Ile His Leu Phe Thr Thr Cys Val Pro Gln His
            260                 265                 270

Asn His Ser Thr His Phe Pro Tyr Leu Asn His Ala Arg His Leu Asn
        275                 280                 285

His Val Leu His Pro Ser His Ala Arg His Pro Asn Leu Ser Ser Thr
    290                 295                 300


<210> SEQ ID NO 17
<211> LENGTH: 304
<212> TYPE: PRT
<213> ORGANISM: African swine fever virus

<400> SEQUENCE: 17

Met Glu Tyr Phe Lys Ser Asn Cys Ile Leu Asn Asn Ile Phe Thr Ile
1               5                   10                  15

Asn Asp Thr Tyr Gly Gly Leu Phe Trp Asn Thr Tyr Tyr Asp Asn Asn
            20                  25                  30

Arg Ser Asn Phe Thr Tyr Cys Gly Ile Ala Gly Asn Tyr Cys Ser Cys
        35                  40                  45

Cys Gly His Asn Ile Ser Leu Tyr Asn Thr Thr Asn Asn Cys Ser Leu
    50                  55                  60

Ile Ile Phe Pro Asn Asn Thr Glu Ile Phe Asn Arg Thr Tyr Glu Leu
65                  70                  75                  80

Val Tyr Leu Asp Lys Lys Ile Asn Tyr Thr Val Lys Leu Leu Lys Ser
                85                  90                  95
```

```
Val Asp Ser Pro Thr Ile Thr Tyr Asn Cys Thr Asn Ser Leu Ile Thr
            100                 105                 110

Cys Lys Asn Asn Asn Gly Thr Asn Val Asn Ile Tyr Leu Ile Ile Asn
        115                 120                 125

Asn Thr Ile Val Asn Asp Thr Asn Gly Asp Ile Leu Asn Tyr Tyr Trp
    130                 135                 140

Asn Gly Asn Asn Asn Phe Thr Ala Thr Cys Met Ile Asn Asn Thr Ile
145                 150                 155                 160

Ser Ser Leu Asn Glu Thr Glu Asn Ile Asn Cys Thr Asn Pro Ile Leu
                165                 170                 175

Lys Tyr Gln Asn Tyr Leu Ser Thr Leu Phe Tyr Ile Ile Ile Phe Ile
            180                 185                 190

Val Ser Gly Leu Ile Ile Gly Ile Phe Ile Ser Ile Ile Ser Val Leu
        195                 200                 205

Ser Ile Arg Arg Lys Arg Lys Lys His Val Glu Glu Ile Glu Ser Pro
    210                 215                 220

Pro Pro Ser Glu Ser Asn Glu Glu Asp Ile Ser His Asp Asp Thr Thr
225                 230                 235                 240

Ser Ile His Glu Pro Ser Pro Glu Asn His Tyr Phe Leu Ser Leu Thr
                245                 250                 255

Val Val Ile Ser Ile Ile His Leu Phe Thr Thr Cys Val Pro Gln His
            260                 265                 270

Asn His Ser Thr His Phe Pro Tyr Leu Asn His Ala Arg His Leu Asn
        275                 280                 285

His Val Leu His Pro Ser His Ala Arg His Pro Asn Leu Ser Ser Thr
    290                 295                 300


<210> SEQ ID NO 18
<211> LENGTH: 370
<212> TYPE: PRT
<213> ORGANISM: African swine fever virus

<400> SEQUENCE: 18

Met Ile Ile Ile Val Ile Phe Leu Met Cys Leu Lys Ile Val Leu Asn
1               5                   10                  15

Asn Ile Ile Ile Trp Ser Thr Leu Asn Gln Thr Val Phe Leu Asn Asn
            20                  25                  30

Ile Phe Thr Ile Asn Asp Thr Tyr Gly Gly Leu Phe Trp Asn Thr Tyr
        35                  40                  45

Tyr Asp Asn Asn Arg Ser Asn Phe Thr Tyr Cys Gly Ile Ala Gly Asn
    50                  55                  60

Tyr Cys Ser Cys Cys Gly His Asn Ile Ser Leu Tyr Asn Thr Thr Asn
65                  70                  75                  80

Asn Cys Ser Leu Ile Ile Phe Pro Asn Asn Thr Lys Ile Phe Asn Arg
                85                  90                  95

Thr Tyr Glu Leu Val Tyr Leu Asp Lys Lys Ile Asn Tyr Thr Val Lys
            100                 105                 110

Leu Leu Lys Ser Val Asp Ser Pro Thr Ile Thr Tyr Asn Cys Thr Asn
        115                 120                 125

Ser Leu Ile Thr Cys Lys Asn Asn Asn Gly Thr Asn Val Asn Ile Tyr
    130                 135                 140

Leu Ile Ile Asn Asn Thr Ile Val Asn Asp Thr Asn Gly Asp Ile Leu
145                 150                 155                 160

Asn Tyr Tyr Trp Asn Gly Asn Asn Asn Phe Thr Ala Thr Cys Met Ile
                165                 170                 175
```

```
Asn Asn Thr Ile Ser Ser Leu Asn Glu Thr Glu Asn Ile Asn Cys Thr
            180                 185                 190

Tyr Pro Ile Leu Lys Tyr Gln Asn Tyr Leu Ser Thr Leu Phe Tyr Ile
        195                 200                 205

Ile Ile Phe Ile Val Ser Gly Leu Ile Ile Gly Ile Phe Ile Ser Ile
    210                 215                 220

Ile Ser Val Leu Ser Ile Arg Arg Lys Lys His Val Glu Glu Ile Glu
225                 230                 235                 240

Ser Pro Pro Pro Ser Glu Ser Asn Glu Glu Asp Ile Ser His Asp Asp
                245                 250                 255

Thr Thr Ser Ile His Glu Pro Ser Pro Arg Glu Pro Leu Leu Pro Lys
            260                 265                 270

Pro Tyr Ser Arg Tyr Gln Tyr Asn Thr Pro Ile Tyr Tyr Met Arg Pro
        275                 280                 285

Ser Thr Gln Pro Leu Asn Pro Phe Pro Leu Pro Lys Pro Cys Pro Pro
    290                 295                 300

Pro Lys Pro Cys Pro Pro Pro Lys Pro Cys Pro Pro Pro Lys Pro Cys
305                 310                 315                 320

Pro Ser Pro Lys Pro Cys Pro Pro Pro Lys Pro Cys Pro Ser Pro Glu
                325                 330                 335

Ser Tyr Ser Pro Pro Lys Pro Leu Pro Asn Ile Pro Leu Leu Pro Asn
            340                 345                 350

Ile Pro Pro Leu Ser Thr Gln Asn Ile Ser Leu Ile His Val Asp Arg
        355                 360                 365

Ile Ile
    370


<210> SEQ ID NO 19
<211> LENGTH: 373
<212> TYPE: PRT
<213> ORGANISM: African swine fever virus

<400> SEQUENCE: 19

Met Ile Ile Ile Val Ile Phe Leu Met Cys Leu Lys Ile Val Leu Asn
1               5                   10                  15

Asn Ile Ile Ile Trp Ser Thr Leu Asn Gln Thr Val Phe Leu Asn Asn
            20                  25                  30

Ile Phe Thr Ile Asn Asp Thr Tyr Gly Gly Leu Phe Trp Asn Thr Tyr
        35                  40                  45

Tyr Asp Asn Asn Arg Ser Asn Phe Thr Tyr Cys Gly Ile Ala Gly Asn
    50                  55                  60

Tyr Cys Ser Cys Cys Gly His Asn Ile Ser Leu Tyr Asn Thr Thr Asn
65                  70                  75                  80

Asn Cys Ser Leu Ile Ile Phe Pro Asn Asn Thr Glu Ile Phe Asn Arg
                85                  90                  95

Thr Tyr Glu Leu Val Tyr Leu Asp Lys Lys Ile Asn Tyr Thr Val Lys
            100                 105                 110

Leu Leu Lys Ser Val Asp Ser Pro Thr Ile Thr Tyr Asn Cys Thr Asn
        115                 120                 125

Ser Leu Ile Thr Cys Lys Asn Asn Asn Gly Thr Asn Val Asn Ile Tyr
    130                 135                 140

Leu Ile Ile Asn Asn Thr Ile Ser Ser Leu Asn Glu Thr Glu Asn Ile
145                 150                 155                 160

Asn Cys Thr Asn Pro Ile Leu Lys Tyr Gln Asn Tyr Leu Ser Thr Leu
```

```
                165                 170                 175

Phe Tyr Ile Ile Ile Phe Ile Val Ser Gly Leu Ile Ile Gly Ile Phe
            180                 185                 190

Ile Ser Ile Ile Ser Val Leu Ser Ile Arg Arg Lys Arg Lys Lys His
        195                 200                 205

Val Glu Glu Ile Glu Ser Pro Pro Pro Ser Glu Ser Asn Glu Glu Asp
    210                 215                 220

Ile Ser His Asp Asp Thr Thr Ser Ile His Glu Pro Ser Pro Arg Glu
225                 230                 235                 240

Pro Leu Leu Pro Lys Pro Tyr Ser Arg Tyr Gln Tyr Asn Thr Pro Ile
                245                 250                 255

Tyr Tyr Met Arg Pro Ser Thr Gln Pro Leu Asn Pro Phe Pro Leu Pro
            260                 265                 270

Lys Pro Cys Pro Pro Pro Lys Pro Cys Pro Pro Pro Lys Pro Cys Pro
        275                 280                 285

Pro Pro Lys Pro Cys Pro Thr Pro Lys Pro Cys Ser Pro Pro Lys Pro
    290                 295                 300

Cys Arg Pro Pro Lys Pro Cys Pro Pro Pro Lys Pro Cys Pro Pro Pro
305                 310                 315                 320

Lys Pro Cys Pro Pro Pro Lys Pro Cys Pro Pro Ser Lys Pro Cys Pro
                325                 330                 335

Ser Pro Glu Ser Tyr Ser Pro Pro Lys Pro Leu Pro Ser Ile Pro Leu
            340                 345                 350

Leu Ser Asn Ile Pro Pro Leu Ser Thr Gln Asn Ile Ser Leu Ile His
        355                 360                 365

Val Asp Arg Ile Ile
    370


<210> SEQ ID NO 20
<211> LENGTH: 394
<212> TYPE: PRT
<213> ORGANISM: African swine fever virus

<400> SEQUENCE: 20

Met Cys Leu Lys Ile Val Leu Asn Asn Ile Ile Ile Trp Ser Thr Leu
1               5                   10                  15

Asn Gln Thr Val Phe Leu Asn Asn Ile Phe Thr Ile Asn Asp Thr Tyr
            20                  25                  30

Gly Gly Leu Phe Trp Asn Thr Tyr Tyr Asp Asn Asn Arg Ser Asn Phe
        35                  40                  45

Thr Tyr Cys Gly Ile Ala Gly Asn Tyr Cys Ser Cys Cys Gly His Asn
    50                  55                  60

Ile Ser Leu Tyr Asn Thr Thr Asn Asn Cys Ser Leu Ile Ile Phe Pro
65                  70                  75                  80

Asn Asn Thr Glu Ile Phe Asn Arg Thr Tyr Glu Leu Val Tyr Leu Asp
                85                  90                  95

Lys Lys Ile Asn Tyr Thr Val Lys Leu Leu Lys Ser Val Asp Ser Pro
            100                 105                 110

Thr Ile Thr Tyr Asn Cys Thr Asn Ser Leu Ile Thr Cys Lys Asn Asn
        115                 120                 125

Asn Gly Thr Asn Val Asn Ile Tyr Leu Ile Ile Asn Asn Thr Ile Val
    130                 135                 140

Asn Asp Thr Asn Gly Asp Ile Leu Asn Tyr Tyr Trp Asn Gly Asn Asn
145                 150                 155                 160
```

```
Asn Phe Thr Ala Thr Cys Met Ile Asn Asn Thr Ile Ser Ser Leu Asn
            165                 170                 175

Glu Thr Glu Asn Ile Asn Cys Thr Asn Pro Ile Leu Lys Tyr Gln Asn
            180                 185                 190

Tyr Leu Ser Thr Leu Phe Tyr Ile Ile Ile Phe Ile Val Ser Gly Leu
        195                 200                 205

Ile Ile Gly Ile Phe Ile Ser Ile Ile Ser Val Leu Ser Ile Arg Arg
    210                 215                 220

Lys Arg Lys Lys His Val Glu Glu Ile Glu Ser Pro Pro Pro Ser Glu
225                 230                 235                 240

Ser Asn Glu Glu Asp Ile Ser His Asp Asp Thr Thr Ser Ile His Glu
            245                 250                 255

Pro Ser Pro Arg Glu Pro Leu Leu Pro Lys Pro Tyr Ser Arg Tyr Gln
            260                 265                 270

Tyr Asn Thr Pro Ile Tyr Tyr Met Arg Pro Ser Thr Gln Pro Leu Asn
        275                 280                 285

Pro Phe Pro Leu Pro Lys Pro Cys Pro Pro Pro Lys Pro Cys Pro Pro
    290                 295                 300

Pro Lys Pro Cys Pro Pro Pro Lys Pro Cys Pro Pro Pro Lys Pro Cys
305                 310                 315                 320

Ser Pro Pro Lys Pro Cys Arg Pro Pro Lys Pro Cys Pro Pro Pro Lys
            325                 330                 335

Pro Cys Pro Pro Pro Lys Pro Cys Pro Pro Pro Lys Pro Cys Pro Pro
            340                 345                 350

Pro Lys Pro Cys Pro Ser Pro Glu Ser Tyr Ser Pro Pro Lys Pro Leu
        355                 360                 365

Pro Ser Ile Pro Leu Leu Pro Asn Ile Pro Pro Leu Ser Thr Gln Asn
    370                 375                 380

Ile Ser Leu Ile His Val Asp Arg Ile Ile
385                 390


<210> SEQ ID NO 21
<211> LENGTH: 402
<212> TYPE: PRT
<213> ORGANISM: African swine fever virus

<400> SEQUENCE: 21

Met Ile Ile Ile Val Ile Phe Leu Met Cys Leu Lys Ile Val Leu Asn
1               5                   10                  15

Asn Ile Ile Ile Trp Ser Thr Leu Asn Gln Thr Val Phe Leu Asn Asn
            20                  25                  30

Ile Phe Thr Ile Asn Asp Thr Tyr Gly Gly Leu Phe Trp Asn Thr Tyr
        35                  40                  45

Tyr Asp Asn Asn Arg Ser Asn Phe Thr Tyr Cys Gly Ile Ala Gly Asn
    50                  55                  60

Tyr Cys Ser Cys Cys Gly His Asn Ile Ser Leu Tyr Asn Thr Thr Asn
65                  70                  75                  80

Asn Cys Ser Leu Ile Ile Phe Pro Asn Asn Thr Glu Ile Phe Asn Arg
            85                  90                  95

Thr Tyr Glu Leu Val Tyr Leu Asp Lys Lys Ile Asn Tyr Thr Val Lys
            100                 105                 110

Leu Leu Lys Ser Val Asp Ser Pro Thr Ile Thr Tyr Asn Cys Thr Asn
        115                 120                 125

Ser Leu Ile Thr Cys Lys Asn Asn Asn Gly Thr Asn Val Asn Ile Tyr
    130                 135                 140
```

```
Leu Ile Ile Asn Asn Thr Ile Val Asn Asp Thr Asn Gly Asp Ile Leu
145                 150                 155                 160

Asn Tyr Tyr Trp Asn Gly Asn Asn Asn Phe Thr Ala Thr Cys Met Ile
                165                 170                 175

Asn Asn Thr Ile Ser Ser Leu Asn Glu Thr Glu Asn Ile Asn Cys Thr
            180                 185                 190

Asn Pro Ile Leu Lys Tyr Gln Asn Tyr Leu Ser Thr Leu Phe Tyr Ile
        195                 200                 205

Ile Ile Phe Ile Val Ser Gly Leu Ile Ile Gly Ile Phe Ile Ser Ile
    210                 215                 220

Ile Ser Val Leu Ser Ile Arg Arg Lys Arg Lys Lys His Val Glu Glu
225                 230                 235                 240

Ile Glu Ser Pro Pro Pro Ser Glu Ser Asn Glu Glu Asp Ile Ser His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Pro Pro Lys Pro Cys Ser Pro Pro Lys Pro Cys Arg Pro
                325                 330                 335

Pro Lys Pro Cys Pro Pro Pro Lys Pro Cys Pro Pro Pro Lys Pro Cys
            340                 345                 350

Pro Pro Pro Lys Pro Cys Pro Pro Ser Lys Pro Cys Pro Ser Pro Glu
        355                 360                 365

Ser Tyr Ser Pro Pro Lys Pro Leu Pro Ser Ile Pro Leu Leu Pro Asn
    370                 375                 380

Ile Pro Pro Leu Ser Thr Gln Asn Ile Ser Leu Ile His Val Asp Arg
385                 390                 395                 400

Ile Ile


<210> SEQ ID NO 22
<211> LENGTH: 402
<212> TYPE: PRT
<213> ORGANISM: African swine fever virus

<400> SEQUENCE: 22

Met Ile Ile Ile Val Ile Phe Leu Met Cys Leu Lys Ile Val Leu Asn
1               5                   10                  15

Asn Ile Ile Ile Trp Ser Thr Leu Asn Gln Thr Val Phe Leu Asn Asn
            20                  25                  30

Ile Phe Thr Ile Asn Asp Thr Tyr Gly Gly Leu Phe Trp Asn Thr Tyr
        35                  40                  45

Tyr Asp Asn Asn Arg Ser Asn Phe Thr Tyr Cys Gly Ile Ala Gly Asn
    50                  55                  60

Tyr Cys Ser Cys Cys Gly His Asn Ile Ser Leu Tyr Asn Thr Thr Asn
65                  70                  75                  80

Asn Cys Ser Leu Ile Ile Phe Pro Asn Asn Thr Glu Ile Phe Asn Arg
                85                  90                  95

Thr Tyr Glu Leu Val Tyr Leu Asp Lys Lys Ile Asn Tyr Thr Val Lys
            100                 105                 110
```

Leu Leu Lys Ser Val Asp Ser Pro Thr Ile Thr Tyr Asn Cys Thr Asn
        115                 120                 125

Ser Leu Ile Thr Cys Lys Asn Asn Asn Gly Thr Asn Val Asn Ile Tyr
    130                 135                 140

Leu Ile Ile Asn Asn Thr Ile Val Asn Asp Thr Asn Gly Asp Ile Leu
145                 150                 155                 160

Asn Tyr Tyr Trp Asn Gly Asn Asn Asn Phe Thr Ala Thr Cys Met Ile
                165                 170                 175

Asn Asn Thr Ile Ser Ser Leu Asn Glu Thr Glu Asn Ile Asn Cys Thr
            180                 185                 190

Asn Pro Ile Leu Lys Tyr Gln Asn Tyr Leu Ser Thr Leu Phe Tyr Ile
        195                 200                 205

Ile Ile Phe Ile Val Ser Gly Leu Ile Ile Gly Ile Phe Ile Ser Ile
    210                 215                 220

Ile Ser Val Leu Ser Ile Arg Arg Lys Arg Lys Lys His Val Glu Glu
225                 230                 235                 240

Ile Glu Ser Pro Pro Pro Ser Glu Ser Asn Glu Glu Asp Ile Ser His
                245                 250                 255

Asp Asp Thr Thr Ser Ile His Glu Pro Ser Pro Arg Glu Pro Leu Leu
            260                 265                 270

Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Pro Pro Lys Pro Cys Ser Pro Pro Lys Pro Cys Arg Pro
                325                 330                 335

Pro Lys Pro Cys Pro Pro Pro Lys Pro Cys Pro Pro Pro Lys Pro Cys
            340                 345                 350

Pro Pro Pro Lys Pro Cys Pro Pro Ser Lys Pro Cys Pro Ser Pro Glu
        355                 360                 365

Ser Tyr Ser Pro Pro Lys Pro Leu Pro Ser Ile Pro Leu Leu Pro Asn
    370                 375                 380

Ile Pro Pro Leu Ser Thr Gln Asn Ile Ser Leu Ile His Val Asp Arg
385                 390                 395                 400

Ile Ile

<210> SEQ ID NO 23
<211> LENGTH: 63
<212> TYPE: PRT
<213> ORGANISM: African swine fever virus

<400> SEQUENCE: 23

Asn Asn Gly Thr Asn Thr Asn Ile Tyr Leu Asn Ile Asn Asp Thr Phe
1               5                   10                  15

Val Lys Tyr Thr Asn Glu Ser Ile Leu Glu Tyr Asn Trp Asn Asn Ser
            20                  25                  30

Asn Ile Asn Asn Phe Thr Ala Thr Cys Ile Ile Asn Asn Thr Ile Ser
        35                  40                  45

Thr Ser Asn Glu Thr Thr Leu Ile Asn Cys Thr Tyr Leu Thr Leu
    50                  55                  60

<210> SEQ ID NO 24

```
<211> LENGTH: 63
<212> TYPE: PRT
<213> ORGANISM: African swine fever virus

<400> SEQUENCE: 24

Asn Ile Asn Asp Thr Phe Val Lys Tyr Thr Asn Glu Ser Ile Leu Glu
1               5                   10                  15

Tyr Asn Trp Asn Asn Ser Asn Ile Asn Asn Phe Thr Ala Thr Cys Ile
            20                  25                  30

Ile Asn Asn Thr Ile Ser Thr Ser Asn Glu Thr Thr Leu Ile Asn Cys
        35                  40                  45

Thr Tyr Leu Thr Leu Ser Ser Asn Tyr Phe Tyr Thr Phe Phe Lys
    50                  55                  60


<210> SEQ ID NO 25
<211> LENGTH: 53
<212> TYPE: PRT
<213> ORGANISM: African swine fever virus

<400> SEQUENCE: 25

Asn Ile Asn Asp Thr Phe Val Lys Tyr Thr Asn Glu Ser Ile Leu Glu
1               5                   10                  15

Tyr Asn Trp Asn Asn Ser Asn Ile Asn Asn Phe Thr Ala Thr Cys Ile
            20                  25                  30

Ile Asn Asn Thr Ile Ser Thr Ser Asn Glu Thr Thr Leu Ile Asn Cys
        35                  40                  45

Thr Tyr Leu Thr Leu
    50
```

AFRICAN SWINE FEVER DIVA IMMUNOASSAY

CROSS-REFERENCE TO RELATED APPLICATIONS

This application is a National Stage application of International Patent Application No. PCT/EP2021/087447, filed Dec. 23, 2021, which claims priority to U.S. Provisional Patent Application No. 20/217,271.4, filed Dec. 24, 2020.

SEQUENCE LISTING

The instant application contains an electronic Sequence Listing which has been submitted in an ASCII plain text file via the Patent Center, the entire content of which is hereby incorporated by reference in its entirety. The Sequence Listing text file submitted via the Patent Center is entitled "25186-FF.txt" and was created on Jun. 9, 2021, and is 73,311 bytes in size.

FIELD OF THE INVENTION

The invention relates to a diagnostic use of an African swine fever virus (ASFV) CD2v antigen, a method, a device, and a kit for the detection of the presence of ASFV antibodies in a test sample

BACKGROUND OF THE INVENTION

The background of the disease African swine fever (ASF), its causative agent: the ASF virus, and attempts to control the virus have been the subject of many recent reviews (Arias et al., Vaccines 5, 35, 2017; Galindo et al., Viruses 9, 103, 2017; Revilla et al., Advances in Vir. Res. 100, 2018; Sanchez et al., Vir. Res. 265, 150-155, 2019; Blome et al., Vir. Res. 287, 98099, 2020; Bosch-Camas et al., Porcine Health Management, 2020 6: 17; Dixon et al., Annu. Rev. Anim. Biosci., 2020, 8:221-246.

In the early 1900s, ASF was reported in East Africa as an acute haemorrhagic fever causing the death of almost all infected domestic pigs. The source of infection was identified as a virus that spread from an ancient sylvatic cycle. Since then, ASFV has spread to most sub-Saharan African countries and Europe. Eradication of the disease was achieved in Europe by the mid-1990s. The 2007 introduction to Georgia in the Caucasus heralded a new transmission era, as ASFV subsequently spread to many, mostly East-European, countries. In 2018, the situation worsened considerably when ASFV was detected in China, which is believed to contain half the world's swine population. The high socio-economic impact of ASF results from animal suffering, loss of business in the pig production chain, costs of disease control, and loss of trade. Large epidemics can result in a dramatic size reduction of national pig herds and inflation of prices of pig and pork products. ASF is listed as a notifiable disease by the World Organisation for Animal Health (OIE).

The host range of ASFV is restricted to suids and to soft ticks of the *Ornithodoros* genus. In its wild suid hosts in Africa, ASFV infection causes mild clinical signs and can result in longer-term persistent infections. In contrast, most ASFV isolates cause an acute haemorrhagic fever, with a case fatality rate approaching 100%, in domestic pigs and wild boar. Disease observed in domestic pigs and wild boar include acute and peracute forms, which are caused by highly virulent isolates and result in death within 4 to 15 days post infection. Moderately virulent isolates cause lower case fatality (30-70%). Low-virulence isolates result in low or no case fatalities and absence of vascular lesions. However, signs of chronic disease, such as joint inflammations, can be observed. The clinical signs of acute ASF include high fever, loss of appetite, and increasing lethargy and morbidity. Bloody diarrhoea, vomiting, and abortion may also be observed.

ASFV is one of the largest- and most complex, cytoplasmic, double-stranded DNA viruses The virus replicates in cells of the mononuclear phagocyte system, mainly monocytes and macrophages, although other cell types can be infected. ASFV virions are icosahedral structures of approximately 200 nm, which are formed by concentric layers, comprising an internal core, a core shell, an inner membrane, a capsid, and, in the extracellular virions, an external envelope. This virus is the only member of the family Asfarviridae, and is classified within the genus Asfivirus.

The ASFV genome varies in length from 170 to 190 kbp among different ASFV strains. This is due to the size variability of several open reading frames (ORFs), especially in the multigene family (MGF) regions of the genome, and to the variation of short tandem repeats within genes and intergenic regions. Depending on the strain, the genome contains 150 to 167 ORFs which are involved in viral replication and morphogenesis as well as in modulation of host cell functions and immune evasion. On the basis of molecular genotyping, 23 distinct genotypes of ASFV have been described to date.

The roles of various ASFV structural- and non-structural proteins in viral infection, immunogenicity and virulence have been investigated in the past and are reviewed in, inter alia, Jia et al., J. Vet. Res. 61, 135-143, 2017; Blome et al., Virus Research 287, 98099, 2020; and Bosch-Camas et al., Porcine Health Management, 2020 6:17. More than 50 proteins are packaged into virus particles, while more than 100 proteins are involved in infection. ASFV proteins under current investigation are i.a. pp220, pp62, p54, p30, p72, p14.5, p17, CD2v, A238Lp, A179Lp, A238Lp, A224Lp, DP71Lp, and proteins encoded by MGFs.

Despite the fact that several research groups during the past few years have developed novel vaccine technologies, ranging from inactivated-, recombinant protein/peptide-, DNA-, and live-attenuated virus (LAV) vaccine candidates, to date, a commercial, efficacious and safe ASFV vaccine does not exist. Hence, presently, only prevention-, control- and eradication measures can be taken to combat ASF disease. These are mainly based on early detection by laboratory diagnosis and on the implementation of strict sanitary measures, movement- and trade restrictions as well as on culling of infected herds. These problems can theoretically be solved through the use of so-called marker vaccines. Such vaccines lack one or more of the immunogenic viral proteins, as a result of which animals immunized with marker vaccines will not produce antibodies against all immunogenic viral proteins. The differences in the ASFV antibody palette between vaccinated and infected animals can be detected in diagnostic tests designed for this purpose. Such tests thus allow for "Differentiating Infected from Vaccinated Animals" (DIVA).

The availability of an effective and safe ASF (marker) vaccine would improve ASF disease control- and eradication programs, thus improving animal welfare and reducing economic losses. However, the complexity of the ASF virus itself and the lack of understanding of the intricacies of protective immunity to ASFV has hampered so far the commercial availability of a safe and effective vaccine.

Although safe, inactivated ASFV vaccines do not confer protection even in the presence of strong adjuvants.

Several attempts to develop ASFV subunit vaccines have been reported (Bosch-Camas et al., 2020, supra). Currently, more than forty ASFV proteins have been investigated. These include proteins such as, p30, p12, p72, p54, p22, CD2v, and D117L. However, vaccines based on immunogenic subunit proteins provided no or only low-, homologous protection against virulent ASFV challenge.

Live attenuated virus (LAV) vaccines are considered to be the most promising type of vaccine to combat ASF. Recently, attempts are made to develop recombinant LAVs based on live, replicating ASFV strains from which genes related to virulence and/or blockage of the host immune response have been inactivated. Examples of ASFV genes targeted for deletion in order to improve the safety of ASFV strains include: DP71L, several MGF 360- and MGF 505 genes, 9GL, DP96R, CD2v, A283L, A224L, EP153R, A276R, DP148R, B119L, and DP96R, among others.

WO 2018/005358 (University of Connecticut) discloses a novel mutant ASFV-G Δ9GL/ΔUK virus, resulting from the deletion of a large portion of both the 9GL (B119L) gene and the UK (DP96R) gene of the parental Georgia 2007 strain.

WO 2020/049194 (University of Madrid) discloses and characterizes a field isolate of ASFV named Lv17/WB/Rie1. This ASFV strain was isolated from an infected wild boar, in Latvia. The new ASFV strain was used as a live attenuated vaccine in wild boar by oral administration and proved to be both safe and efficacious.

US 2020/0129609 (Pirbright Institute) discloses the deletion of five MGF 360 genes 10L, 11 L, 12L, 13L, 14L and three MGF505 genes 1R, 2R, 3R as well as the interruption of additional genes (MGF360 9L, MGF 505 4R and DP148R). These mutations resulted in the attenuation of a virulent virus and vaccination with the new mutant strain inducted 100% protection against challenge with the parental ASFV strain.

It is generally accepted that in order to successfully combat the present world-wide ASFV epidemic, an additional requirement for a truly efficient vaccination strategy has to be fulfilled besides the availability of a safe and efficacious vaccine, namely: the availability of a diagnostic assay that allows for reliable DIVA approach. In general, a DIVA diagnostic assay is a diagnostic assay designed and adapted such that it can be used in conjunction with a safe and efficacious DIVA vaccine. Together, such an assay and accompanying vaccine make it possible to eradicate a disease based on immunologic prophylaxis and infection surveillance. Basically, the active component in a DIVA vaccine displays a phenotypic/genotypic characteristic that differs from that of the pathogen circulating in the field (negative marker).

According to the European Union Reference Laboratory for ASF (eurl-asf), currently, PCR is considered the 'gold standard' test for early detection of the disease due to its superior sensitivity, specificity, robustness, and high throughput application to detect the ASFV genome in any kind of clinical samples from domestic pigs, pigs, wild boar, and ticks. Over the last twenty years, a variety of PCR tests, including both conventional and real-time PCR assays, have been developed and validated to detect a wide range of ASF isolates belonging to different known virus genotypes. All of these PCR assays have been designed using the VP72-coding region, a highly conserved gene coding the major viral protein, assuring the (potential) detection of any ASFV isolate.

Detection of specific antibodies against ASFV by ELISA is the OIE-prescribed test for international trade so far. Currently, a number of ASF ELISA variants is available as well as several OIE "in house" versions of the test based on the use of live virus as antigen. Three commercial ELISA kits (INGENASA, IDVET and SVANOVIR) are validated and available for the detection of anti-ASFV antibodies. These ELISA assays are based on the most antigenic proteins described so far, such as: p72, p32, pp62, and p54 (see https://asf-referencelab.info/asf/en/procedures-diagnosis/diagnostic-procedures).

Kollnberger et al., (J. Gen. Virol. 83, 1331-1342, 2002) identified the principal serological immune-determinants of ASFV by ELISA screening of expressed ASFV proteins with convalescent antiserum and identified 14 viral proteins that stimulated an antibody response that was recognized in the ELISA. These included six proteins encoded by previously unassigned ORFs (B602L, C44L, CP312R, E184L, K145R, and K205R), as well as some of the more well-studied structural- (A104R, p10, p32, p54, and p73) and non-structural proteins (RNA reductase F334Lp, F778Rp, DNA ligase (NP419Lp), and thymidine kinase (K169Rp)).

In WO 2020/102370 ASFV diagnostic antigens were validated using ASFV convalescent serum. A chimeric antigen designated KP1712 was recognized more strongly than p32, p54, p72, and pp62, which have previously been evaluated as diagnostic antigens.

However, none of the above documents identified an ASFV protein that can be used as an antigen in a diagnostic assay on the one hand, and that can be used as an accompanying marker immunogen in a marker vaccine on the other hand that allows DIVA.

It is therefore an object of the present invention to provide an in vitro diagnostic assay capable of serologically distinguishing between a sample from an animal that was vaccinated with an ASFV marker vaccine and a sample from an animal infected with an ASFV circulating in the field.

LEGENDS TO THE FIGURES

FIG. 1

Schematic representation of the full length ASFV CD2v protein, its domains and fragments used in the Examples. The numbering is based on GenBank acc. no. CAD2068420.

FIG. 2

ASFV CD2v protein amino acid sequence alignments of various ASFV strains.

Visualization of alignment with MView: https://www.ebi.ac.uk/Tools/msa/mview/.

Nrs. 1-8 are genotype II strains, serogroup 8 CD2v.

Nrs. 9-15 are genotype I strains, serogroup 4 CD2v.

Figure 2:
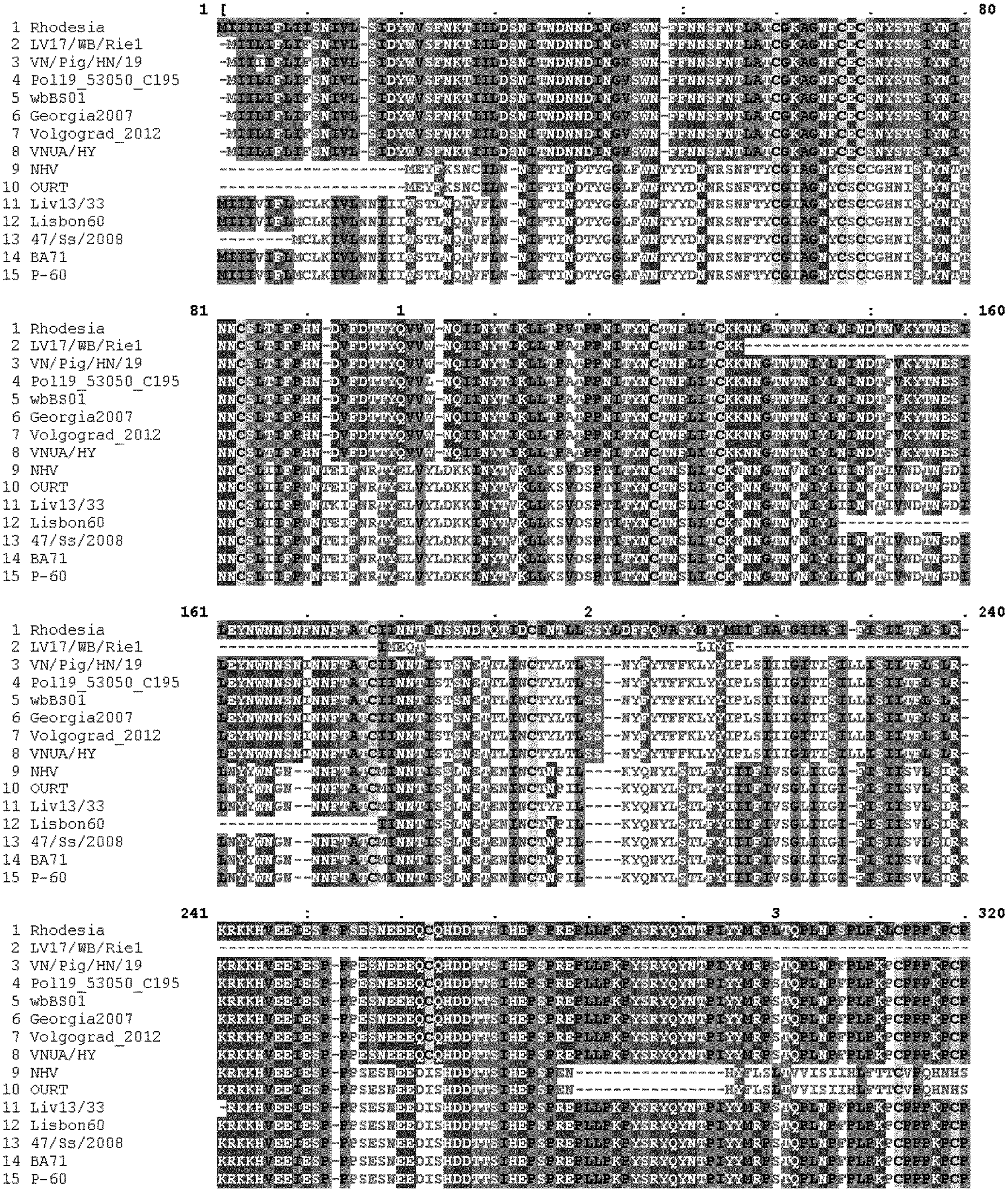

The concordance to the SEQ ID numbers is given below:

| Fig. 2 nr. | Name | GenBank acc.nr. | aa nrs. start-end | SEQ ID NO: |
|---|---|---|---|---|
| 1 | Rhodesia | AJB28392.1 | 1-375 | 8 |
| 2 | LV17/WB/Riel | — | 1-140 | 9 |
| 3 | VN/Pig/HN/19 | QEH60630.1 | 1-360 | 10 |

-continued

| Fig. 2 nr. | Name | GenBank acc.nr. | aa nrs. start-end | SEQ ID NO: |
|---|---|---|---|---|
| 4 | Pol19_53050_C195 | QOW03114.1 | 1-360 | 11 |
| 5 | wbBS01 | QDL88089.1 | 1-360 | 12 |
| 6 | Georgia2007 | YP_009927182.1 | 1-360 | 13 |
| 7 | Volgograd_2012 | AJB28407.1 | 1-360 | 14 |
| 8 | VNUA/HY | QCS27843.1 | 1-360 | 15 |
| 9 | NHV | YP_009702625.1 | 1-304 | 16 |
| 10 | OURT | YP_009703666.1 | 1-304 | 17 |
| 11 | Liv13/33 | QID21219.1 | 1-370 | 18 |
| 12 | Lisbon60 | AAM90854.1 | 1-373 | 19 |
| 13 | 47/Ss/2008 | YP_009703302.1 | 1-394 | 20 |
| 14 | BA71 | NP_042752.1 | 1-402 | 21 |
| 15 | P-60 | AJB28388.1 | 1-402 | 22 |

FIG. 3

Relative optical densities measured at 450 nm in ELISA (CD2 "16-204" antigen) for various serum samples.

FIG. 4

Relative optical densities measured at 450 nm in ELISA (CD2 "132-204" antigen) for various serum samples.

FIG. 5

Relative optical densities measured at 450 nm in ELISA (CD2 "132-204" antigen) for various serum samples.

FIG. 6

ELISA optical densities measured at 450 nm (CD2 "132-204" antigen) at several serum sample dilutions in various sample diluents.

FIG. 7

The effect of the size of the CD2v fragment on ELISA performance. ELISA optical densities were measured at 450 nm using CD2v fragments of different length, and different serum samples which were diluted at 1:300.

NB: The CD2v fragment 132-204 was not tested with sera S13, S15, S19 or S21, for lack of peptide material.

FIG. 8

The effect of detergent concentration in the sample diluent on the P/N ratio of the ELISA. The CD2v peptide fragment used was CD2 "132-204", and a series of dilutions of the various serum samples.

FIG. 9

The effect of salt concentration in the sample diluent on the P/N ratio of the ELISA. The CD2 "132-204" peptide was used, and several dilutions of serum samples.

NB: The datapoints for the C-67 serum are fully overlapped by those of the S3 serum.

FIG. 10

The effect of PBS buffer in the sample diluent on the P/N ratio of the ELISA. The CD2 "132-204" peptide was used, and several dilutions of serum samples.

DESCRIPTION OF THE INVENTION

Surprisingly, it was found that this object can be met by an in vitro diagnostic immunoassay for the detection of anti-ASFV antibodies wherein the assay is based on an isolated ASFV CD2v antigen.

The observation that an isolated ASFV CD2v antigen can be used to effectively distinguish between ASFV infected animals and animals vaccinated with an ASFV (CD2-) marker vaccine, for the first time now, allows the implementation of a DIVA strategy to combat the epidemic.

An important step towards this advantageous observation was the recognition by the inventors that, despite reports in the prior art that the ASFV CD2v protein is a weak immunogen (Ruiz-Gonzalvo et al., Virology 196, 769-777, 1993; Argilaguet et al., PLoS ONE 7(9): e40942. doi:10.1371/journal.pone.0040942; Gomez-Puertas et al., J. of Virol. August 1996, p. 5689-5694; Lokhandwala et al., Vet. Micr. 235, 10-20, 2019 and PLoS ONE 12(5): e0177007. https://doi.org/10.1371/journal.pone.0177007, 2017), an isolated ASFV CD2v antigen can advantageously be used in an immunoassay for the purpose of the present invention.

A test sample obtained from an animal vaccinated with an accompanying LAV CD2v-marker vaccine can be serologically distinguished from a test sample obtained from an animal infected with a wild-type ASFV strain, with the required specificity and sensitivity (Examples 1-3). This observation allows for the first time to combat the ASF epidemic with a DIVA strategy the veterinary field has long been waiting for.

The Examples also show that in a CD2v-antigen based antibody ELISA, convalescent ASFV swine antiserum could not be distinguished from an ASFV negative control swine serum sample with confidence, as a result of the occurrence of non-specific binding of components in anti-ASFV antiserum with an ASFV CD2v antigen in an immunoassay. Treatment of the convalescent swine serum sample with a sample diluent revealed that (i) the CD2v protein of the ASFV can be used in an immunoassay as an antigen to detect the presence or absence of anti-CD2v antibodies in a swine test sample, with sufficient specificity and sensitivity, (ii) the ASFV gene encoding the CD2v protein (EP402R) is an appropriate target for genetic modification resulting in a LAV ASFV strain that can be used as a DIVA vaccine, (iii) the CD2v protein in wild-type ASFV is of sufficient immunogenicity to induce a detectable anti-CD2v antibody response in swine and (iv) modified LAV ASFV can accompany the immunoassay in advantageous diagnostic protocols allowing DIVA.

Therefore, in a first aspect the invention provides a use of an isolated African swine fever virus (ASFV) CD2v protein or an antigenic fragment thereof, bound to a solid support, as an antigen in an immunoassay, characterized in that the CD2v protein or antigenic fragment thereof is used to detect the presence (that includes the absence) of ASFV antibodies in a test sample obtained from a swine vaccinated with an accompanying ASFV live attenuated virus CD2v-marker vaccine (LAV CD2v-marker vaccine).

ASFV CD2v protein is a known- and well-established ASFV protein (Borca et al., Virology 199, 463-468, 1994; Rodriguez et al., J. Gen. Virol. 67, 5312-5320, 1993). It is a glycoprotein with a relative molecular weight of about 105 kDa that is responsible for the haemadsorption phenotype of ASFV infected cells in vitro and is encoded by the EP402R gene on the ASFV genome. This ASFV protein is the viral homolog (CD2v) of cellular T-lymphocyte surface adhesion receptor CD2 proteins. Based on sequence data and hydropathy profiles, ASFV CD2v protein resembles typical (CD2) class III transmembrane proteins. Generally, the full-length ASFV CD2v protein contains four different sections: (i) a hydrophobic leader at the N-terminal side of the protein, (ii) a hydrophilic, extracellular domain comprising a multitude of potential N-linked glycosylation sites, (iii) a hydrophobic stretch of amino acids that act as a transmembrane domain, and (iv) a C-terminal hydrophilic, cytoplasmic domain which contains a large number of typical, imperfect repeats of the hexa peptide (PPPKPC) (FIG. 1). Detailed information regarding ASFV CD2v protein and the EP402 gene of a large number of ASFV strains, including the genomic location of the ASFV genes, (alignment of) nucleotide/amino acid sequence information, identification of the four CD2v domains and other annotations, can be found in FIG. 2 and the various public nucleic acid- and protein sequence data bases, such as the NCBI genome database, UniProt, EMBL/GenBank and the European Union reference laboratory for African Swine Fever (EURL-ASF) at Centro de investigacion en sanidad animal (CISA-INIA) (https://asf-referencelab.info/asf/en/sequence-database). In Zhu and Meng (Database, 1-9, 2020) the authors report the establishment of an ASFV database wherein the collective public genomic- and proteomic ASFV information is collected and made available. ASFVdb is freely accessible at http://asfvdb.popgenetics.net and viruSITE genome browser; http://virusite.org/index.php, Stano, M., Beke, G., Klucar, L. (2016): viruSITE—integrated database for viral genomics. Database (Oxford). baw162.doi: 10.1093/database/baw162.

The sequences of CD2v ASFV proteins and their polypeptide fragments used herein can vary from the specific sequences disclosed herein. This is due to the existing natural sequence variation among ASFV strains, as is apparent from the sequences available from the above-mentioned public sequence databases and FIG. 2. The specific CD2v amino sequence and specific sequence numbering described herein relate to the ASFV reference strain Georgia 2007/1 and is also disclosed in GenBank under acc. No. CAD2068420 (SEQ ID NO: 1) The complete genomic nucleotide sequence and amino acid sequences of the polypeptides encoded by the Georgia 2007/1 genome are also shown in GenBank, under accession no. FR682468.

In particular, the ASFV CD2v protein used herein is defined as a protein comprising an extracellular domain comprising an amino acid sequence with at least 95% amino acid sequence identity to SEQ ID NO: 2 (CD2 "16-204"), preferably at least 99% amino acid sequence identity to SEQ ID NO: 2 or 100% sequence identity, in the regions of overlap (alignment with MUSCLE algorithm www.ebi.ac.ukfTools/msa/muscle/).

In the context of the present invention an antigenic fragment of an ASFV CD2v protein as described above can also be used as the antigen. Such an antigenic fragment represents a truncated from of the CD2v protein and is a polypeptide comprising one or more epitopes that can be recognized by anti-ASFV CD2v antibodies in a test sample obtained from a swine infected with a wild-type ASFV.

Preferably, the antigenic fragment is a polypeptide comprising an extracellular domain of the CD2v protein or an antigenic fragment of the extracellular domain.

An extracellular domain of an ASFV CD2v protein is located at the N-terminal side of a transmembrane domain.

An extracellular domain or transmembrane domain of an ASFV CD2v protein can be identified on the basis of its typical amino acid sequence by methods know in the art, such as described by Kyte and Doolittle (J. Mol. Biol. 157, 105-132) and Rodriguez et al., (J. Virol. 67, 5312-5320, 1993). Alternatively, such domains are disclosed in the public sequence databases for known ASFV strains or can be identified by amino acid sequence alignment with one or more of the amino acid sequences of ASFV extracellular domains available from the public sequence databases. For example, the four domains of the Georgia 2007/1 CD2v protein span approximately the following amino acid regions: leader: aa 1-15; extracellular domain: aa 16-204; transmembrane region: aa 205-229; and extracellular domain: aa 230-360, whereby the amino acid numbers are indicated in relation to the numbering of the reference amino acid sequence SEQ ID NO: 1.

In a particularly preferred embodiment an extracellular domain of an ASFV CD2v protein comprises an amino acid sequence with at least 95% amino acid sequence identity to SEQ ID NO: 2, preferably at least 99% amino acid sequence identity to SEQ ID NO: 2 or 100% amino acid sequence identity, in the regions of overlap.

In another preferred embodiment, an antigenic fragment of the extracellular domain for use in the present invention is a polypeptide comprising an amino acid sequence with at least 95% amino acid sequence identity to SEQ ID NO: 3 (CD2 "132-204"), preferably at least 99% amino acid sequence identity to SEQ ID NO: 3 or 100% amino acid sequence identity, in the regions of overlap.

In a more preferred embodiment, an antigenic fragment of the extracellular domain for use in the present invention is a polypeptide comprising an amino acid sequence with at least 95% amino acid sequence identity to a sequence selected from SEQ ID NO: 23 and 24; even more preferably at least 99% amino acid sequence identity to a sequence selected from SEQ ID NO: 23 and 24; still more preferably 100% amino acid sequence identity to a sequence selected from SEQ ID NO: 23 and 24, in the regions of overlap.

In a most preferred embodiment, an antigenic fragment of the extracellular domain for use in the present invention is a polypeptide comprising an amino acid sequence with at least 95% amino acid sequence identity to SEQ ID NO: 25; even more preferably at least 99% amino acid sequence identity to SEQ ID NO: 25; still more preferably 100% amino acid sequence identity to SEQ ID NO: 25, in the regions of overlap.

For the invention, SEQ ID NO: 3 is CD2 "132-204"; SEQ ID NO: 23 is CD2 "132-194"; SEQ ID NO: 24 is CD2 "142-204"; and SEQ ID NO: 25 is CD2 "142-194".

In the Examples, it is shown that in case the CD2 "132-204" fragment of the extracellular domain (of a genotype II strain) is used as an antigen in an ELISA, also genotype I positive test samples react with this antigen, whereas it is also shown that the complete extracellular polypeptide CD2 "16-204" is not recognized by antibodies in genotype I positive samples. Thus, the CD2 "132-204" fragment can advantageously be used according to the invention in a DIVA immunoassay for serologically distinguishing between samples from swine vaccinated by either genotype I or genotype II accompanying LAV strains, and samples from swine infected with wild-type ASFV containing an intact CD2v gene.

Therefore, in an even more preferred embodiment an antigenic fragment of the extracellular domain used herein is a polypeptide comprising an ASFV amino acid sequence consisting of an amino acid sequence with at least 95% amino acid sequence identity to SEQ ID NO: 3 (CD2 "132-204"), preferably at least 99% amino acid sequence identity to SEQ ID NO: 3 or 100% amino acid sequence identity, in the regions of overlap.

In a yet even more preferred embodiment, an antigenic fragment of the extracellular domain used herein is a polypeptide comprising an ASFV amino acid sequence consisting of an amino acid sequence with at least 95% amino acid sequence identity to a sequence selected from SEQ ID NO: 23 and 24; more preferably at least 99% amino acid sequence identity to a sequence selected from SEQ ID NO: 23 and 24; still more preferably 100% amino acid sequence identity to a sequence selected from SEQ ID NO: 23 and 24, in the regions of overlap.

In a most preferred embodiment, an antigenic fragment of the extracellular domain used herein is a polypeptide comprising an ASFV amino acid sequence consisting of an amino acid sequence with at least 95% amino acid sequence identity to SEQ ID NO: 25; more preferably at least 99% amino acid sequence identity to SEQ ID NO: 25; still more preferably 100% amino acid sequence identity to SEQ ID NO: 25, in the regions of overlap.

Alternatively, an antigenic fragment of the extracellular domain used herein is a polypeptide comprising an ASFV amino acid sequence consisting of an amino acid sequence with at least 95%, at least 99% or 100% amino acid sequence identity, in the regions of overlap, to any of the fragments 132-194, 132-214, 122-194, 122-204 or 142-214, as shown in SEQ ID NO: 1; as well as to any of the fragments 132-194, 142-204, or 142-194, as shown in SEQ ID NO: 1.

An ASFV CD2v antigen as described above can be of any serogroup known for ASF viruses, in particular of serogroup 4 or 8, preferably of serogroup 8.

ASFV serogroup clustering is based on examining the inhibition of the ASFV haemadsorption phenotype by serum belonging to the same group. Presently, the existence of serogroups 1-8 is established (Malogolovkin et al., J. Gen. Virol. 96, 866-873, 2015).

Furthermore, an ASFV CD2v antigen as described above may comprise a tag to allow the detection of protein expression or purification of the antigen. Suitable tags include a 6×His tag, a c-Myc domain: EQKLISEEDL (SEQ ID NO: 4), a hemagglutinin tag: YPYDVPDYA (SEQ ID NO: 5), a maltose-binding protein, a glutathione-S-transferase, a maltose-binding protein, a FLAG tag peptide, a biotin acceptor peptide, a streptavidin-binding peptide, or a calmodulin-binding peptide, as disclosed in Chatterjee (Opin. Biotech 17, 353-358, 2006). A FLAG tag or His tag is a preferred tag.

For the manufacture of a CD2v antigen used herein, common- and commercially available conventional peptide synthesis methods and -recombinant DNA expression systems and methods can be used, that include bacterial-, yeast-, fungal-, insect- and vertebrate cell expression systems. Ample guidance with regard to prokaryotic- and eukaryotic expression systems is given i.a. in reviews and text books on recombinant DNA expression methods such as: Trepe, K., Applied Microbiology and Biotechnology, 72, Number 2 (2006), 211-222; Production of Recombinant Proteins: Novel Microbial and Eukaryotic Expression Systems, edited by Gellissen, G. Publisher: Wiley-VCR, ISBN: 3527310363 edition 2005, Expression systems, edited by Michael Dyson and Yves Durocher, Scion Publishing Ltd, ISBN 9781904842439 edition 2007.

Advantageously, a CD2v antigen can be prepared by using a Baculovirus-insect cell expression system. Examples of scientific articles, text-books, and reviews illustrating this system are: Luckow et al., 1988, Bio-technology, vol. 6, p. 47; Baculovirus Expression Vectors: A Laboratory Manual by David R. O'Reilly, Oxford University press, 1993, ISBN: 0716770172; The Baculovirus Expression System: A laboratory guide, ed. King & Possee, 1992, ISBN: 9401050473; and a review is: van Oers et al., 2015, J. of Gen. Virology, 96, 6-23. Expression and purification of ASFV polypeptides in *E. coli*- and insect cell systems are, for example, described in Lokhandwala et al., PLOS ONE, May 2017, and Kollnberger et al. (supra).

Tools and kits are commercially available for the efficient generation of baculoviruses for use in the present invention, such as: Bac-to-Bac™ (Thermo Fisher Sci., Waltham, MA., USA); ProEasy™ (AB Vector, San Diego, CA., USA); and flashBAC™ (Oxford Expression Technologies, Oxford, UK).

A "marker vaccine" is a well-known concept in the veterinary vaccinology field. A marker vaccine comprises- and/or expresses an altered polypeptide immunogen that differs immunogenically from the corresponding wild-type polypeptide immunogen by lacking at least one epitope, or having a different version of an epitope, as compared to the wild-type version. Typically, the (gene encoding the) polypeptide immunogen in- or expressed by the marker vaccine has been altered by biochemical- or recombinant DNA techniques, and the result is that the lack of an antibody response against a wild-type moiety in the altered immunogen in the marker vaccine can be used to serologically detect infected animals independent of vaccinations. This will allow a serologic DIVA. Typically, the altered immunogen is an immunogen that is absent, or is a fragment of the wildtype polypeptide immunogen.

The term immunogen as used herein refers to a molecule's (such as a protein or polypeptide) capability of eliciting a specific antibody response by an organism's immune system, whereas the term antigen refers to a molecule's capability of specific binding to antibodies produced by an organism's immune system.

An epitope as used herein is a stretch of, typically 5-15, amino acids within a protein or polypeptide that is capable of eliciting an antibody response specific for this moiety and/or of binding with the specific antibodies produced by such a response.

A LAV CD2v-marker vaccine as used herein is a vaccine that comprises a live, attenuated, replicating ASFV marker vaccine strain that is capable of expressing an altered CD2v polypeptide immunogen that is serological distinguishable from a CD2v polypeptide immunogen of a wild-type ASFV strain.

With an "accompanying" LAV CD2v-marker vaccine is meant a vaccine comprising a CD2v marker vaccine strain as defined above and wherein an altered CD2v polypeptide immunogen is aligned with—and designed to be different from a CD2v polypeptide antigen in an immunoassay such that the CD2v polypeptide antigen is serologically capable of detecting antibodies in a test sample specific for a wild-type moiety of a CD2v polypeptide immunogen and is not capable of recognizing antibodies specific for an altered moiety of a CD2v polypeptide immunogen.

Thus, an accompanying LAV CD2v-marker vaccine comprises a CD2v-marker vaccine strain, as defined above, that triggers an effective immune response in swine resulting in an antibody repertoire in a serum sample of a vaccinated swine lacking antibodies that are present in an antibody repertoire in a serum sample of a swine infected with a wild-type ASFV. Differentiating between infected- and vaccinated- or negative animals is thus based on an immunoassay detecting antibodies specific for one or more ASFV CD2v epitopes that are missing in the marker vaccine.

In particular, the accompanying LAV CD2v-marker vaccine comprises an ASFV CD2v-marker vaccine strain that comprises and/or is capable of expressing a truncated CD2v protein or no CD2v protein. Preferably, the truncated CD2v protein is a polypeptide fragment of the CD2v protein that lacks an extracellular domain or a fragment thereof.

More preferably, the truncated CD2v protein is a polypeptide fragment of the CD2v protein that lacks a fragment of the extracellular domain.

In an even more preferred embodiment, the truncated CD2v protein is a polypeptide fragment of the CD2v protein that lacks a fragment of the extracellular domain of the CD2v protein, comprising an amino acid sequence with at least 95% amino acid sequence identity to SEQ ID NO: 3 (CD2 "132-204"), preferably at least 99% amino acid sequence identity to SEQ ID NO: 3 or 100% amino acid sequence identity, in the regions of overlap.

In a yet even more preferred embodiment, the truncated CD2v protein is a polypeptide fragment of the CD2v protein that lacks a fragment of the extracellular domain of the CD2v protein, comprising an amino acid sequence with at least 95% amino acid sequence identity to a sequence selected from SEQ ID NO: 23 and 24; even more preferably at least 99% amino acid sequence identity to a sequence selected from SEQ ID NO: 23 and 24; still more preferably 100% amino acid sequence identity to a sequence selected from SEQ ID NO: 23 and 24, in the regions of overlap.

In a most preferred embodiment, the truncated CD2v protein is a polypeptide fragment of the CD2v protein that lacks a fragment of the extracellular domain of the CD2v protein, comprising an amino acid sequence with at least 95% amino acid sequence identity to SEQ ID NO: 25; even more preferably at least 99% amino acid sequence identity to SEQ ID NO: 25; still more preferably 100% amino acid sequence identity to SEQ ID NO: 25, in the regions of overlap.

In a still more preferred embodiment, the truncated CD2v protein is a polypeptide fragment of the CD2v protein that lacks a fragment of the extracellular domain of the CD2v protein, that comprises an ASFV amino acid sequence consisting of an amino acid sequence with at least 95% amino acid sequence identity to SEQ ID NO: 3 (CD2 "132-204"), preferably at least 99% amino acid sequence identity to SEQ ID NO: 3 or 100% amino acid sequence identity, in the regions of overlap.

In an even still more preferred embodiment, the truncated CD2v protein is a polypeptide fragment of the CD2v protein that lacks a fragment of the extracellular domain of the CD2v protein, that comprises an ASFV amino acid sequence consisting of an amino acid sequence with at least 95% amino acid sequence identity to a sequence selected from SEQ ID NO: 23 and 24; more preferably at least 99 (Y0 amino acid sequence identity to a sequence selected from SEQ ID NO: 23 and 24; still more preferably 100% amino acid sequence identity to a sequence selected from SEQ ID NO: 23 and 24, in the regions of overlap.

In a most preferred embodiment, the truncated CD2v protein is a polypeptide fragment of the CD2v protein that lacks a fragment of the extracellular domain of the CD2v protein, that comprises an ASFV amino acid sequence consisting of an amino acid sequence with at least 95% amino acid sequence identity to SEQ ID NO: 25; more preferably at least 99% amino acid sequence identity to SEQ ID NO: 25; still more preferably 100% amino acid sequence identity to SEQ ID NO: 25, in the regions of overlap.

In a specific embodiment of the use of a ASFV CD2v antigen in an immunoassay, as described above, detecting the presence (including the absence) of ASFV antibodies in a test sample obtained from a swine vaccinated with the accompanying LAV CD2v-marker vaccine, the ASFV CD2v antigen has no epitope in common, and, in particular, no overlapping amino acid sequence, with the altered CD2v polypeptide immunogen of—or expressed by the CD2v-marker vaccine strain. With no overlapping amino acid sequence is meant that the ASFV CD2v antigen in the immunoassay and the altered CD2v polypeptide immunogen of—or expressed by the LAV CD2v-marker vaccine strain are from different regions of the CD2v protein and show no overlap at their termini.

More preferably, an ASFV CD2v antigen in the immunoassay and an altered CD2v polypeptide immunogen in the accompanying marker vaccine, as described above, represent two different, non-overlapping, fragments of an extracellular domain of an ASFV CD2v protein.

Suitable live-attenuated ASFV CD2v-marker vaccine strains are known in the art or can be prepared by recombinant DNA techniques using standard methods, such as CRISPR-Cas or homologous recombination, or can be isolated from the field.

Recently, results of various research activities have been published that disclose the (rational) design of ASFV LAV strains by means of genetically modifying ASFV strains (see ASFV review articles, supra, and references cited therein). These prior art documents disclose a variety of ASFV genes that can be mutated to arrive at attenuated- and efficacious ASFV vaccine strains.

The prior art also discloses the generation of various ASFV mutant strains that comprise- or express altered CD2v proteins: Gallardo et al. (Transbound. Emerg. Dis. 66, 1399-1404, 2019) and Barasona et al. (Front. Vet. Sci. 6; 137, 2019). ASFV strain Lv17/WB/Rie1 (WO 2020/049194) has been tested for its safety and efficacy profile after immunization of domestic pigs and wild boar. Lv17/WB/Rie1 is a naturally attenuated strain that has a truncated CD2v protein (encoded by a mutant EP402R gene) and has a non-haemadsorbing phenotype in vitro. Another naturally occurring, non-pathogenic ASFV isolate, OURT88/3, comprises frameshift mutations in the sequence encoding the cytoplasmic domain of CD2v that result in the final 215 amino acids not being translated. Borca et al. (J. Virol. 72, 2881-2889, 1998 and Sci Rep. 2020, 10:494) and Monteagudo et al. (J. Virol. 91, 2017, 91(21):e01058-17) disclose the generation of a CD2v deletion mutant by means of recombinant DNA techniques, based on ASFV strains Malawi, Georgia 2007/1 and BA71, respectively. Chen et al. (Sci China Life Sci, 63, 2020) discloses the generation of a seven-gene deleted ASFV strain (HLJ/18) that is effective and safe as a live-attenuated virus vaccine in swine. Among other deletions, also the gene encoding the CD2v protein is deleted in HLJ/18.

An ASFV CD2v antigen and ASFV CD2v-marker vaccine strain to be used in the present invention may be derived from any ASFV genotype or any ASFV strain, such as one of the following strains: Georgia 2007/1, Benin 97/1, Kenyan and Malawi. Preferred ASFV genotypes are I or II. ASFV genotyping is based on genetically characterizing an ASFV genome through partial sequencing of the C-terminal end of the p72 protein (encoded by the B646L gene) which represents the ASFV major capsid protein. This method has defined 24 different genotypes to date (Bastos et al., Arch. Virol. 2003 April; 148:693-706. 2003; Quembo et al., Transbound. Emerg. Dis.; 65, 420-431, 2018).

In a preferred embodiment, the accompanying LAV CD2v-marker vaccine is based on ASFV strain Lv17/WB/

Rie1, disclosed in WO 2020/049194, and the ASFV CD2v antigen is a polypeptide comprising an ASFV amino acid sequence consisting of an amino acid sequence with at least 95% amino acid sequence identity to SEQ ID NO: 3 (CD2 "132-204"), preferably at least 99% amino acid sequence identity to SEQ ID NO: 3 or 100% amino acid sequence identity, in the regions of overlap.

In a more preferred embodiment, the accompanying LAV CD2v-marker vaccine is based on ASFV strain Lv17/WB/Rie1, disclosed in WO 2020/049194, and the ASFV CD2v antigen is a polypeptide comprising an ASFV amino acid sequence consisting of an amino acid sequence with at least 95% amino acid sequence identity to a sequence selected from SEQ ID NO: 23 and 24; even more preferably at least 99 (Y0 amino acid sequence identity to a sequence selected from SEQ ID NO: 23 and 24; still more preferably 100% amino acid sequence identity to a sequence selected from SEQ ID NO: 23 and 24, in the regions of overlap.

In a most preferred embodiment, the accompanying LAV CD2v-marker vaccine is based on ASFV strain Lv17/WB/Rie1, disclosed in WO 2020/049194, and the ASFV CD2v antigen is a polypeptide comprising an ASFV amino acid sequence consisting of an amino acid sequence with at least 95% amino acid sequence identity to SEQ ID NO: 25; even more preferably at least 99% amino acid sequence identity to SEQ ID NO: 25; still more preferably 100% amino acid sequence identity to SEQ ID NO: 25, in the regions of overlap.

An accompanying LAV CD2v-marker vaccine to be used in the present invention can be prepared by conventional methods such as those commonly used for commercially available live-attenuated virus vaccines. Briefly, a susceptible substrate is inoculated with a live-attenuated CD2v-marker vaccine strain as described above and propagated until the virus has replicated to a desired titre after which ASFV containing material is harvested. Subsequently, the harvested material, purified and/or concentrated, if needed, together with a pharmaceutically acceptable carrier or diluent are formulated into a pharmaceutical preparation with immunizing properties. Carriers include stabilizers, preservatives and buffers. Suitable stabilizers are, for example SPGA (sucrose, phosphate, glutamate, and albumin), carbohydrates (such as sorbitol, mannitol, starch, sucrose, dextran, glutamate or glucose), proteins (such as dried milk serum, albumin or casein) or degradation products thereof. Suitable buffers are for example PBS-, Tris- or HEPES buffers. Suitable preservatives are thimerosal, merthiolate and gentamicin.

The vaccine may be administered by intramuscular-, subcutaneous-, intradermal-, oral- or intranasal inoculation or injection, in an amount which is effective to protect a swine against ASF disease. This amount may vary according to the animal being inoculated, taking into consideration the age and weight of the animal In the Examples it is demonstrated that for the first time a successful ASFV DIVA approach has been established by the combined use of a DIVA diagnostic assay and an accompanying DIVA LAV CD2v-marker vaccine, both as defined above. The inventors determined, on the one hand, that ASFV CD2v represents an appropriate immunogen in wild-type ASFV and, on the other hand, that ASFV CD2v also represents an appropriate antigen that can be used in an immunoassay with the required specificity and sensitivity to allow DIVA. A DIVA method as described above allows for vaccination while still retaining the possibility of serological surveillance for the presence of infection, thereby providing for the first time a powerful- and practical tool to combat ASF in animals that can easily be scaled-up, inter alia because the method does not involve the use of live infectious ASFV that would require performing such a method in high containment facilities.

Therefore, in a particular embodiment, an ASFV CD2v antigen as described above is used in an immunoassay, characterized in that the immunoassay is a DIVA immunoassay.

Generally, in order to make a final differentiation between infected and vaccinated animals, test scores need to be interpreted as being positive or negative. In practice that means: being above or below a certain threshold value. This can conveniently be done by incorporating into the method a number of reference samples to be tested alongside the test samples, as for example described in the Examples. Positive and negative reference samples can be prepared in swine, or can be obtained from several institutions, and (national) reference laboratories world-wide, for example the European Union Reference Laboratory for ASFV, Centro de investigacion en sanidad animal (CISA-INIA), Madrid, Spain.

The solid support to be used in an immunoassay as described above can in principle be any solid support, provided it allows the performance of the use according to the invention, in particular: the binding of an ASFV CD2v antigen as described above to the solid support. It can be of different size, shape or form. Binding can occur via conventional means, such as by covalent- or by non-covalent interaction (i.a. adsorption or coating). Alternatively, binding can be achieved through biotinylated CD2v antigen linked to an avidin-coated solid support.

In particular, the solid support is a microtiter plate, vial, bead paper strip, membrane, gel or lateral flow strip. Preferably the solid support is a microtitre plate.

In a further aspect the present invention provides a method for distinguishing between ASFV infected animals (positive test result) and vaccinated animals (negative test result) wherein the method is an immunoassay, characterized in that an isolated ASFV CD2v protein or an antigenic fragment thereof, as described above, that is bound to a solid support is used as an antigen, the marker vaccine is an accompanying LAV CD2v-marker vaccine and the method comprises a step of examining a test sample obtained from the animal for the presence of ASFV CD2v antibodies that bind to the antigen.

In this additional aspect of the invention and embodiments hereof, the definition of the specific terms referred to herein and the various embodiments of this aspect are the same as those described for the first aspect above.

In an embodiment of this aspect the invention provides a method as outlined above wherein the antigenic fragment is a polypeptide comprising an extracellular domain of the CD2v protein or an antigenic fragment of the extracellular domain, more in particular, the antigenic fragment of the extracellular domain is a polypeptide comprising an amino acid sequence with at least 95% amino acid sequence identity to SEQ ID NO: 3 (CD2 "132-204"), even more in particular, the antigenic fragment of the extracellular domain comprises an ASFV amino acid sequence consisting of an amino acid sequence with at least 95% amino acid sequence identity to SEQ ID NO: 3 (CD2 "132-204"), in the regions of overlap.

In a preferred embodiment of this aspect the antigenic fragment of the extracellular domain is a polypeptide comprising an amino acid sequence with at least 95% amino acid sequence identity to a sequence selected from SEQ ID NO: 23 and 24; even more preferably at least 99% amino acid sequence identity to a sequence selected from SEQ ID NO: 23 and 24; still more preferably 100% amino acid sequence identity to a sequence selected from SEQ ID NO: 23 and 24, in the regions of overlap.

In a most preferred embodiment of this aspect the antigenic fragment of the extracellular domain is a polypeptide comprising an amino acid sequence with at least 95% amino acid sequence identity to SEQ ID NO: 25; even more preferably at least 99% amino acid sequence identity to SEQ ID NO: 25; still more preferably 100% amino acid sequence identity to SEQ ID NO: 25, in the regions of overlap.

In a further embodiment of this aspect the invention provides a method as outlined above wherein the accompanying LAV CD2v-marker vaccine comprises an ASFV CD2v-marker vaccine strain that comprises and/or expresses an altered CD2v polypeptide immunogen, more in particular the altered CD2v polypeptide immunogen lacks an extracellular domain of the CD2v protein or a fragment thereof, or the ASFV CD2v antigen and the altered CD2v polypeptide immunogen have no overlapping amino acid sequence, all as defined above.

The design of an immunoassay to be used in the various aspects of this invention, as described above, is similar to commonly used immunoassays that are based on solid support-bound antigen. In principle, the immunoassay is based on the formation of an antibody-antigen complex followed by the subsequent examination of the presence (including the absence) of such a complex. Handbooks, such as those mentioned below, describe a variety of diagnostics assays and their specific features that can be used herein (Handbook of Immunoassay Technologies, by Vashist, Sandeep K. and Luong, John H. T., 2018; and: Immunoassays: Development, Applications and Future Trends, by R. O'Kennedy, C. Murphy 2017).

Detailed information regarding the set-up, protocols, standard operating procedures, reagents, and the like, for ASFV immunoassays to be used in the present invention are also disclosed, for example, by the European Union Reference Laboratory for ASFV (supra)., the FAO (Beltran-Alcrudo et al., 2017, African swine fever: detection and diagnosis—A manual for veterinarians. FAO Animal Production and Health Manual No. 19, Rome) and in: Gallardo et al., Virus Research 271, 197676, 2019.

In a more specific embodiment of the method according to the invention the method comprises the steps of:

1. incubating the test sample with the antigen in an assay mixture,
2. allowing formation of an ASFV CD2v antibody-antigen complex in the assay mixture, and
3. detecting the presence of the antibody-antigen complex in the assay mixture.

In this embodiment, detecting the presence of an antibody-antigen complex, may involve the use of a detecting antibody conjugated to a label.

In particular, it may involve contacting the complex with the antibody-label conjugate.

The nature of the label is not critical and can be any label customarily used in immunoassays. The label is an entity that provides for-, or is capable of triggering a detectable signal.

In particular, the label is an enzyme, fluorophore, chromophore, radioisotope, enzymatic substrate, chemiluminescent molecule, or colloidal gold.

Preferably, the label is an enzyme that can be directly- or indirectly conjugated to the detecting antibody, in particular by biotin/avidin conjugation.

Typically, the enzyme used herein is horseradish peroxidase (HRP) and the enzyme substrate is TMB (3,3',5.5' tetramethylbenzidine).

In a particularly preferred embodiment of the invention as described above, the immunoassay is an ELISA (enzyme linked immunosorbent assay). Advantages of an ELISA include its practicality, reliability, swiftness and easiness to scale-up.

ELISA's are well known in the art, and a variety of types in format and protocols can be applied herein.

An immunoassay as described above may be based upon direct- or indirect antigen-antibody reactions. A direct assay comprises a one-step binding of a sample antibody to the antigen. An indirect assay comprises a two-step binding process involving the use of a primary (sample) antibody and a labelled secondary (detection) antibody capable of binding to the primary antibody. The immunoassay can also be a competitive immunoassay in which antibodies in a sample compete for a limited number of antigen binding sites with labelled secondary antibody capable of binding to the antigen.

In a preferred method according to the present invention as described above, an indirect ELISA is used comprising the steps of:

1. incubating a test sample with solid support-bound antigen in an assay mixture,
2. adding a labelled antibody capable of recognizing anti-ASFV CD2v antibody to the assay mixture,
3. adding an enzyme substrate to the assay mixture to produce a detectable signal, and
4. measuring the signal.

When a chromogenic substrate is added to the assay mixture to develop colour, samples with a high antibody concentration generate a higher signal than those containing a lower antibody concentration.

In a further preferred method according to the present invention as described above, a competition ELISA is used comprising the steps of, 1. incubating a test sample and an antibody capable of binding to the antigen with solid support-bound antigen in an assay mixture,
2. adding an enzyme substrate to the assay mixture to produce a detectable signal, and
3. measuring the signal.

When chromogenic substrate is added to the assay mixture to develop colour, samples with a high antibody concentration generate a lower signal than those containing low antibody concentration, yielding the inverse correlation between antibody concentration in the sample and colour development in the assay.

ELISA results are usually expressed in arbitrary units of absorbance, typically between 0.1 and 2.5 optical density (OD) units, depending on the properties and settings of the technical equipment used for the readout. Routinely, appropriate positive- and negative control samples are included, and most-times samples are tested in multifold. Standardisation is obtained by including (a dilution range of) a defined reference sample, which also allows matching a certain score to pre-set threshold values for determining positives or negatives, and allows correlation to a biological meaning, for example: the discrimination between an animal being infected by a wild-type virus or being vaccinated with a marker-vaccine.

A particularly preferred ELISA is shown in the Examples.

In an alternative method according to the present invention the immunoassay is a lateral flow (immunochromatographic) assay. Lateral flow immunoassays are commonly used in the art. In principle, a lateral flow immunoassay operates on the same principle as an ELISA as described above.

In a lateral flow immunoassay to be used in the present invention, the antigen, as described above, can be bound as a test line to a solid support having the capacity to transport fluid as a result of capillary activity, such as porous paper or (nitrocellulose) membrane, microstructured polymer, or sintered polymer. In essence, the solid support runs sample liquid of the test sample containing the antibody to be detected from an absorption zone along the surface of the support. An antibody-antigen complex can then be formed at the test line and detected in a detection zone of the solid support where the antigen is bound to the solid support.

Therefore, in a particular embodiment of the method of the invention, the immunoassay used herein is a lateral flow immunoassay.

More in particular, the lateral flow immunoassay comprises the steps of:

1. incubating the test sample with the solid support in an absorption zone,
2. allowing the formation of an antibody-antibody/label complex,
3. allowing the movement of the complex laterally through the solid support,
4. capturing the complex by an antigen bound to the solid support at a test line thereby allowing the formation of an antibody-antigen-antibody/label complex, and
5. detecting the presence of the complex in an assay mixture in a detecting zone.

The label used in the lateral flow immunoassay can be any label customary used in LF immunoassays, and can, in particular, be a coloured particle, such as a latex-, nanometre sized- or gold particle, a fluorescent-, magnetic labelled- or radio frequency identification (RFID) particle.

An LF immunoassay used herein can operate as either a competitive- or a sandwich assay.

The inventors initially observed that when an ASFV CD2v antibody positive serum test sample was incubated with a CD2v antigen in an ELISA the signal-to-noise ratio was suboptimal, as a result of which the specificity of the ELISA was negatively affected and no reliable DIVA immunoassay could result from this. It was subsequently found that this limitation was due to short term intermolecular interactions unrelated to the specific antigen-antibody interaction. The Examples demonstrate that this negative effect could be overcome by incorporating a dilution (of the swine antiserum) step in the immunoassay that limits these non-specific intermolecular interactions. Sample diluents that can be used in this step display an increased stringency.

The term stringency of a sample diluent is defined herein as a number that represents a ratio between an absorption value (OD unit) of a diluted positive serum control sample/ an absorption value (OD unit) of a diluted negative serum control sample (P/N ratio) as measured in an ELISA, in particular as described in the Examples.

Therefore, in an advantageous method of the invention the swine test sample is diluted with a sample diluent of an optimal stringency sufficient to limit undesired non-specific interactions without affecting specific antigen-antibody interactions to an undesired level.

A sample diluent to be used in the present invention may have a stringency P/N ratio of 5 or more, preferably of 10 or more as measured in an ELISA.

The Examples demonstrate and provide further guidance that, and how, both incorporating a sample dilution step and increasing the stringency of the sample diluents, allows a CD2v antigen-based immunoassay as defined above to become a reliable DIVA immunoassay. The sample dilution step decreases the non-specific interactions between anti-swine ASFV antiserum and the CD2v antigen in the Elisa and, thus the increase of the P/N ratio and can be designed by the skilled person by using appropriate sample diluents of increased stringency, such that at the same time the Elisa (OD) signal for the positive control sample is maintained at an appropriate level.

Sample diluents that can advantageously be used in a method of the present invention may comprise customary buffers, such as PBS- or TRIS buffers to which surfactants, such as Tween™ 20 or Tween 80, Triton, Na-deoxycholate, sodium dodecyl sulphate, an aminoxide or CHAP detergent, are added.

In a preferred embodiment of the method for distinguishing according to the invention, or alternatively in a preferred embodiment of the method for determining according to the invention, the sample diluent comprises one or more of the surfactants selected from Tween™ 20, Tween 80, and an aminoxide. Preferably the aminoxide is Aminoxide WS 35, also known as: cocamidopropylamine oxide. More preferably the Aminoxide WS 35 is a compound with CAS nr. 53988-60-6.

In a preferred embodiment the surfactant is comprised in the sample diluent at between 1 and 5% w/v; more preferably at 2-4% w/v, or even at 3% w/v.

Therefore, in a preferred embodiment of the invention the method according to the invention comprises a step wherein the test sample is diluted with a sample diluent that has a stringency resulting in a P/N ratio of ≥5, preferably ≥10.

Advantageous P/N ratios can also be obtained by diluting the swine test sample with the sample diluent in ratio of 1:100 to 1:2700, preferably in a ratio of 1:100 to 1:900, more preferably in a ratio of 1:100 to 1:300, more in particular, in a ratio of 1:300.

In further preferred method according to the invention the swine test sample is diluted with a sample diluent that has a stringency resulting in a P/N ratio of 5, preferably 10 and at a dilution in ratio of 1:100 to 1:2700, preferably in a ratio of 1:100 to 1:900, more preferably in a ratio of 1:100 to 1:300, more in particular, in a ratio of 1:300.

In a preferred embodiment of the method for distinguishing according to the invention, or alternatively in a preferred embodiment of the method for determining according to the invention, the sample diluent comprises a salt at between 0.01 and 1 M. More preferably at between 0.05 and 0.5 M, even more preferably at 0.1 M.

In a preferred embodiment the salt is magnesium chloride.

In a most preferred embodiment the sample diluent comprises Tween, aminoxide, and magnesium chloride.

The various aspects of the present invention as outlined above can advantageously be applied by testing a sample derived from a swine that is susceptible to infection with ASFV. Specifically, a swine is a porcine animal of the family of Suidae, and preferably a porcine animal of the genus *Sus*, for example, a pig or wild boar. Preferably the swine is a domestic pig.

Therefore, in a preferred embodiment of the various aspects of the invention, the test sample is derived from a domestic pig.

The test sample for use in the various aspects of the present invention can, in principle, be any type of sample from a swine possibly containing anti-ASFV CD2v antibodies, for example a plasma- or a serum sample. Preferably the sample is a serum sample.

Another aspect of the invention is a device for use in a method for detecting the presence of ASFV CD2v antibodies in a test sample obtained from a swine vaccinated with an accompanying LAV CD2v-marker vaccine as described above, the device comprising an isolated ASFV CD2v antigen bound to a solid support, as described above.

A further aspect of the present invention is a diagnostic kit comprising a device as described above.

A diagnostic kit according to the invention can comprise a single packaging unit that comprises additional components to be applied in a method according to the present invention.

In particular, the diagnostic kit additionally comprises one or more containers comprising:

a sample diluent, an antibody-label conjugate, a positive control sample, and/or a negative control sample.

In a more particular embodiment, the diagnostic kit described above also comprises instructions for use of the kit with a test sample obtained from a swine that is vaccinated with an accompanying LAV CD2v-marker vaccine as described above.

In particular, the instructions for use describe that the diagnostic kit can be used for DIVA and that a test sample from an ASFV infected swine will be positive in that test, in contrast to a test sample from a vaccinated non-infected swine that will be negative.

EXAMPLES

Example 1—ASFV CD2v-Based ELISA

To verify if anti-CD2v antibodies in pig serum can be detected by ELISA, an ELISA was performed using a fragment of the ASFV CD2v protein, referred to as CD2 "16-204". CD2 "16-204" spans the extracellular domain and lacks the leader sequence, the transmembrane domain and the proline-rich intracellular part of the full-length CD2v protein (FIG. 1). It contains a GP64 signal peptide: MVSAIVLYVLLAAAAHSAFA (SEQ ID NO: 6) at its N-terminus and a 6×His-tag at its C-terminus. It was produced by Baculovirus expression and subsequent purification by GenScript.

Serum samples were obtained from the European Union Reference Laboratory for African Swine Fever (CISA-INIA, Spain).

For the ELISA, a 96-well microtiter plate was coated overnight at 2-8° C. with a solution containing the CD2v fragment at a concentration of 1 μg/ml. Plates were washed four times with wash buffer (0.04 M PBS+0.15% Tween20) before they were blocked with casein for 1 hour at 37° C. After washing the plates 4 times, 3-fold serial dilutions of serum samples in EIA buffer (0.2 M PBS+0.1% BSA) were prepared in well A to well G of each column (well H only contained EIA buffer and functioned as a control). Serum samples were pre-diluted 1:100 in EIA buffer. Plates with serum dilutions were incubated for 1 hour at 37° C. and subsequently washed 4 times with wash buffer. To each well a solution with a peroxidase-labelled goat anti-swine IgG (H+L) antibody was added and plates were incubated for 1 hour at 37° C. after which they were washed 4 times with wash buffer. Then a 3,3',5,5'-tetramethylbenzidine (TMB) substrate solution was added to each well and incubated for at least 10 min. The colouring reaction was stopped by adding 4N H2504. Optical densities were measured at 450 nm with a microtiter plate reader and data analysed.

Figure 3:
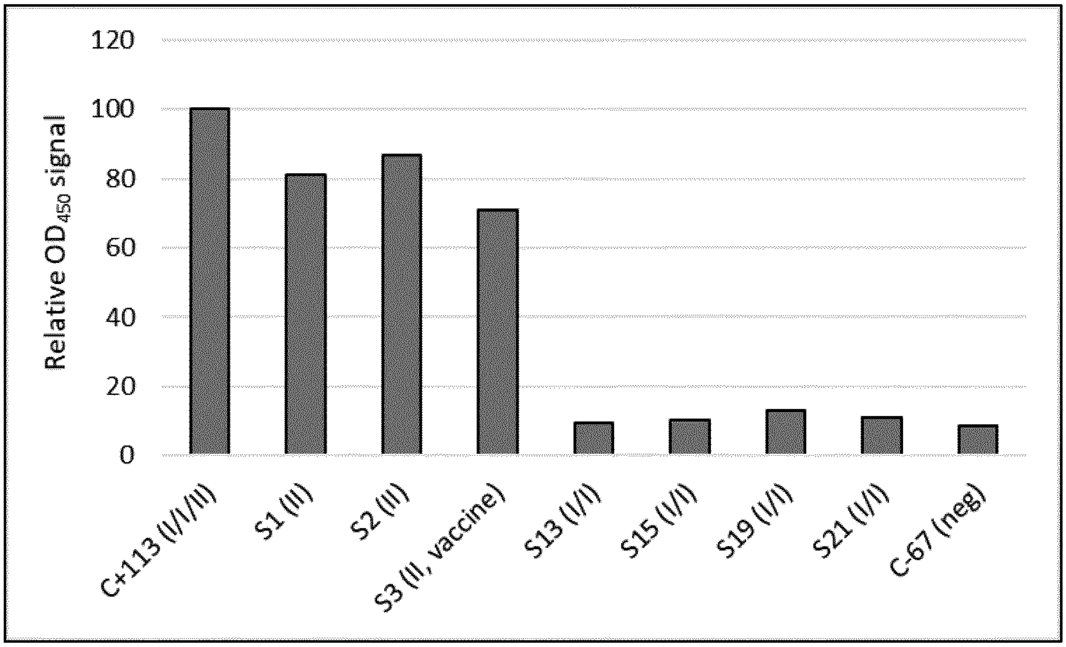

The results are presented in FIG. 3. Sera from swine infected with genotype II ASFV, serotype 8 strains (51, S2, and S3-ASFV strain Lv17/WB/Rie1; WO 2020/049194) displayed at a serum dilution of 1:900 a clear positive signal above the negative serum C-67. Serum sample C+113, obtained from a swine that was infected twice with a genotype I ASFV strain and subsequently also with a genotype II strain, gave a clear positive signal that was set at 100%. Sera from swine infected with genotype I, serotype 4 ASFV strains (S13, S15, S19, S21) could not be distinguished from the negative serum control. Thus, the results demonstrate that CD2v is immunogenic and that an ELISA based on the CD2 "16-204" fragment can be used to measure anti-CD2v antibodies induced by genotype II ASFV strains.

Example 2—CD2v-Based ELISA for the Detection of Genotype I and II ASFV Strains A truncated version of the CD2 "16-204" extracellular CD2v fragment was designed. This fragment, CD2 "132-204" lacks the N-terminal 131 amino acids of the CD2v protein (FIG. 1). It contains at its C-terminus a 5× GlyGlyGlySer (SEQ ID NO: 7) linker followed by a Flag-tag, and was produced by Baculovirus expression and subsequent purification by GenScript.

The ELISA was performed as described in Example 1.

Figure 4:
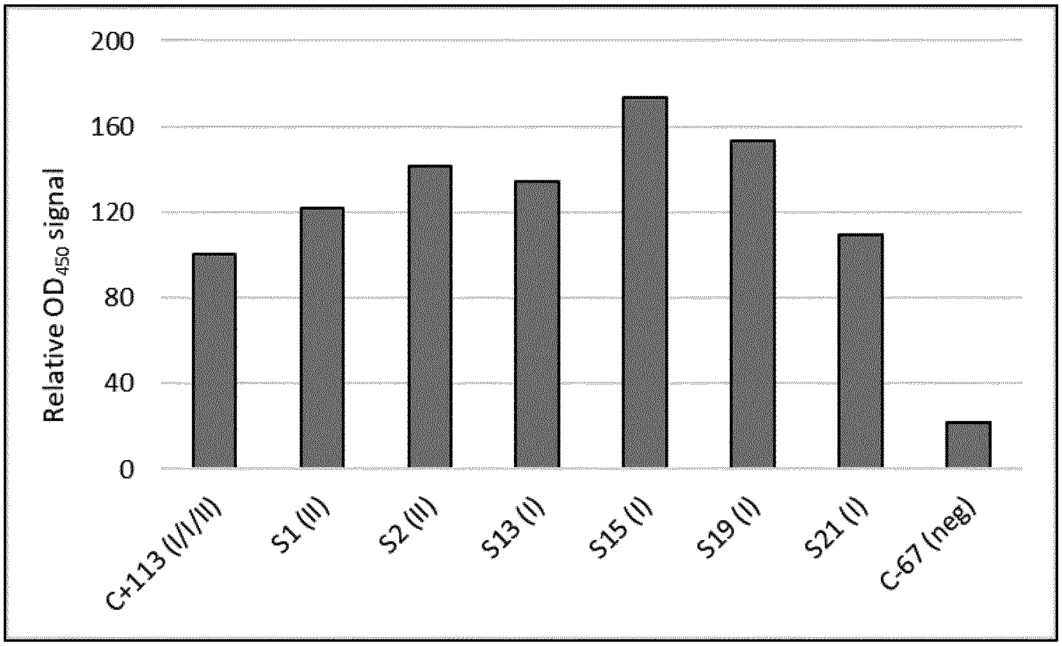

The results are presented in FIG. 4. Sera from swine infected with genotype II ASFV strains (51 and S2) or genotype I ASFV strains (S13, S15, S19, S21) all showed at a serum dilution of 1:300 a clear positive signal above the negative serum C-67. Serum sample C+113 gave also a clear positive signal that was set at 100%. Thus, an ELISA based on the CD2 "132-204" fragment can be used to measure anti-CD2v antibodies induced by either genotype I/serotype 4 or genotype II/serotype 8 ASFV strains.

Example 3—CD2v-Based ELISA as a DIVA Immunoassay

Figure 5:
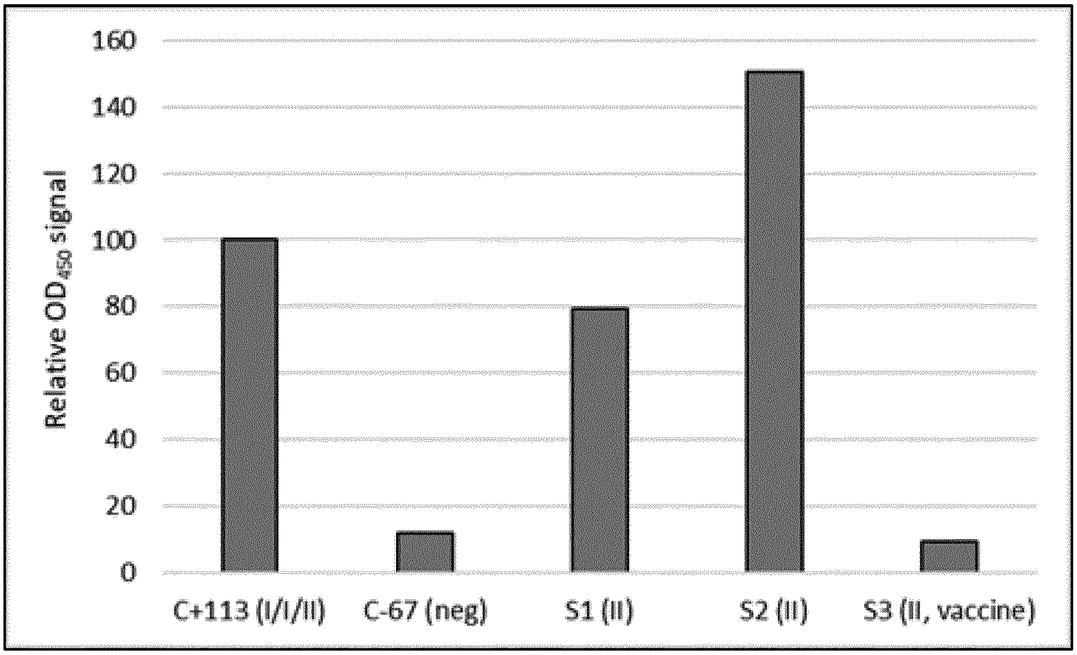

The CD2v fragment that was used in Example 2, CD2 "132-204", was also used in this experiment. The ELISA was performed as described in Example 1, but the sera were diluted (1:300) in 0.04 M PBS+0.05% v/v Tween20 instead of in EIA buffer. CD2v-positive serum samples C+113, 51 and S2, and the negative serum sample C-67 were included in the ELISA. Serum sample S3 was also included, which is derived from a swine that was immunized with the Ly17/WB/Rie1 vaccine strain (that only express the first 131 amino acids of CD2v). The results are presented in FIG. 5. The OD450 value obtained with the C+113 serum sample at a serum dilution of 1:300 was set at 100%. Sera from swine infected with non-vaccine genotype II strains containing intact EP402R genes (C+113, 51 and S2) showed a clear positive signal well above the negative serum C-67. However, the serum sample derived from the Ly17/WB/Rie1-immunized swine (S3) generated a signal similar to the negative control serum. This is in contrast to the observation made in Example 1 that anti-CD2v antibodies are present in sample S3. It can be explained by the fact that anti-CD2v antibodies in sample S3 are directed against the part in CD2 "16-204" that does not overlap with CD2 "132-204". Therefore, the data confirms that vaccine strain Ly17/WB/Rie1 cannot induce antibodies against CD2 "132-204". Thus, an ELISA based on the CD2 "132-204" fragment can be used to differentiate ASFV-infected animals from ASFV-vaccinated animals if the ASF vaccine does not induce antibodies that react with the CD2 "132-204" fragment.

Example 4—Effect of Sample Diluent

The effect of sample diluent on the signal-to-noise ratio was investigated in this example.

A

In this experiment CD2v fragment CD2 "132-204" was used. The ELISA was performed as described in Example 1 but the sera were diluted either in EIA buffer 0.04 M PBS+0.2 M NaCl+0.1% w/v BSA), EIA/T (EIA+0.05% v/v Tween 20), PBS/T (0.04 M PBS+0.15 M NaCl+0.05% v/v Tween 20) or a low metal-salt, high detergent (LSHD) buffer that contains: 3% v/v Tween 20, 3% v/v Aminoxide WS 35, and 0.1 M magnesium-chloride, and does not contain a phosphate buffer. The CD2v-positive serum sample C+113 and the negative serum sample C-67 were included in the ELISA as well as serum sample S3 (derived from an animal infected with the Lv17/WB/Rie1 vaccine strain). Fora reliable DIVA immunoassay, the OD450 values for the S3 sample should be similar to that of the negative serum sample C-67.

Figure 6:
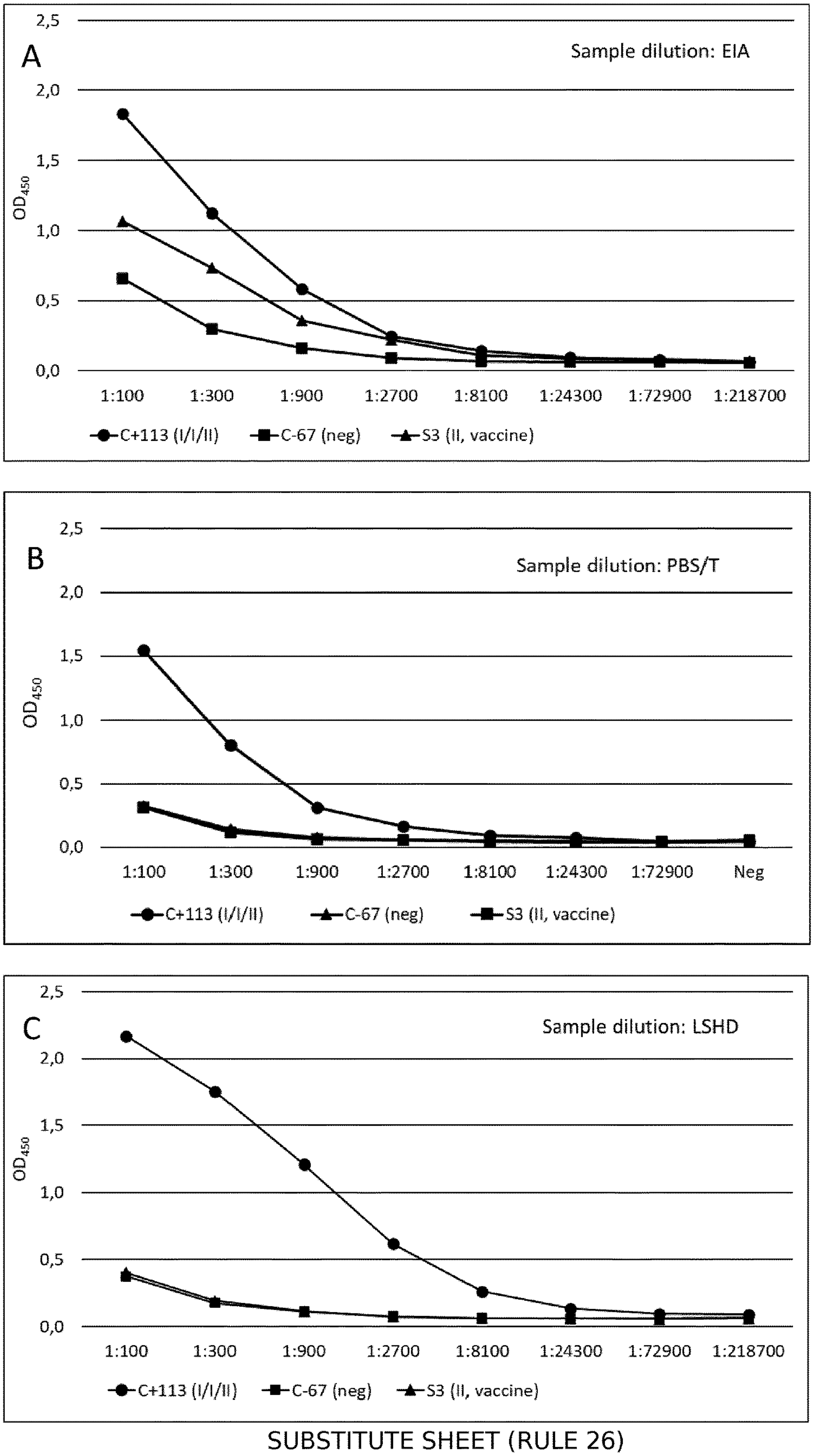

FIG. 6A shows that EIA, a buffer without detergent and with a relatively high salt concentration, provides poor separation of the sample dilution curves. And the OD450 signal of S3 is clearly above that of C-67, meaning that EIA is not an appropriate buffer for a CD2-based DIVA ELISA. By using a low salt buffer containing a low concentration of detergent as the sample diluent, PBS/T, the assay can be improved (FIG. 6B): The dilution curve of sample S3 overlaps with that of the negative serum sample, however, the OD450 values of C+113 are a bit lower than with EIA. The P/N ration is 5.7. To further separate the positive signal from the negative signals, a LSHD buffer was evaluated (FIG. 6C). LSHD as sample diluent provides the most optimal signal-to-noise ratio among the three buffers (P/N ratio 10.3), allowing the clear separation of samples that should be negative in the assay from samples that should give a positive signal. Thus, an ELISA based on the CD2 "132-204" fragment can be used in combination with a low-salt, high detergent buffer to differentiate ASFV-infected animals from ASFV-vaccinated animals.

The addition of urea to the EIA/T sample diluent decreased the P/N ratios mainly due to reduced signals for the positive control.

B

In this experiment, CD2v fragment CD2 "16-204" was used. The ELISA was performed as described in Example 1. The stringency of sample diluents varied by increasing the content of surfactant and metal salts. The stringencies of the three sample diluents used were 2.9, 5.7 and 9.9 respectively. Table 1 demonstrates that only when a sample diluent having a stringency of 5.7 or more resulted in a clear distinction between the OD value of the negative control sample compared to the OD of the vaccine test sample.

TABLE 1

| Relative stringency of | OD serum test samples | | | | | ratio | |
|---|---|---|---|---|---|---|---|
| sample diluent | C + 113 | S1 | S2 | S3 | NC (C − 67) | C + 113/NC | S3/NC |
| low | 2.679 | 2.493 | 2.396 | 2.538 | 0.934 | 2.9 | 2.7 |
| medium | 2.285 | 1.814 | 2.277 | 1.773 | 0.403 | 5.7 | 4.4 |
| high | 1.787 | 1.092 | 1.143 | 0.886 | 0.180 | 9.9 | 4.9 |

C

In this experiment, CD2v fragment CD2 "132-204" was used. The ELISA was performed as described in Example 1. The same sample diluents of experiment B and EIA sample diluent were used. Serum samples were diluted as shown in Table 2. Testing 1/100 dilution of the sera the sample diluent of high stringency results in a P/N ratio of 5.8 and the serum from the vaccinated animal (S3) is as negative as the negative control whereas the noise (0.4) is relatively high.

Testing 1/300 dilution of the sera with this sample diluent results in a P/N ratio of 10.0 and the serum from the vaccinated animal (S3) is as negative as the negative control and the noise (<0.2) is low. The P/N results obtained with the other sample diluents were less satisfactory (<5) for all dilutions.

TABLE 2

| Sample | OD serum test samples | | | | | ratio |
|---|---|---|---|---|---|---|
| dilutions | C + 113 | S1 | S2 | S3 | NC (C − 67) | C + 113/NC |
| 1:100 | 2.167 | 1.691 | 2.046 | 0.403 | 0.376 | 5.8 |
| 1:300 | 1.752 | 1.111 | 2.151 | 0.194 | 0.176 | 10.0 |
| 1:900 | 1.210 | 0.620 | 1.615 | 0.113 | 0.111 | 10.9 |
| 1:2700 | 0.618 | 0.301 | 0.943 | 0.073 | 0.077 | 8.0 |
| 1:8100 | 0.261 | 0.151 | 0.468 | 0.062 | 0.063 | 4.1 |
| 1:24300 | 0.133 | 0.091 | 0.210 | 0.061 | 0.060 | 2.2 |
| 1:72900 | 0.094 | 0.068 | 0.112 | 0.055 | 0.060 | 1.6 |
| 1:218700 | 0.089 | 0.054 | 0.057 | 0.061 | 0.064 | 1.4 |

Example 5—Further Characterisation of CD2v Fragment Size for Use in the ELISA

Several shorter and longer versions of the CD2 "132-204" extracellular CD2v fragment were designed. These fragments were contained amino acids: "122-204", "142-204", "132-194", "132-214", or "122-194" from CD2v. In addition these fragments had at their C-termini the linker of SEQ ID NO: 7, followed by a Flag-tag. The peptide fragments were produced by baculovirus expression and subsequent purification by GenScript, as described in Example 2.

The ELISA was performed as described in Example 1.

Figure 7:
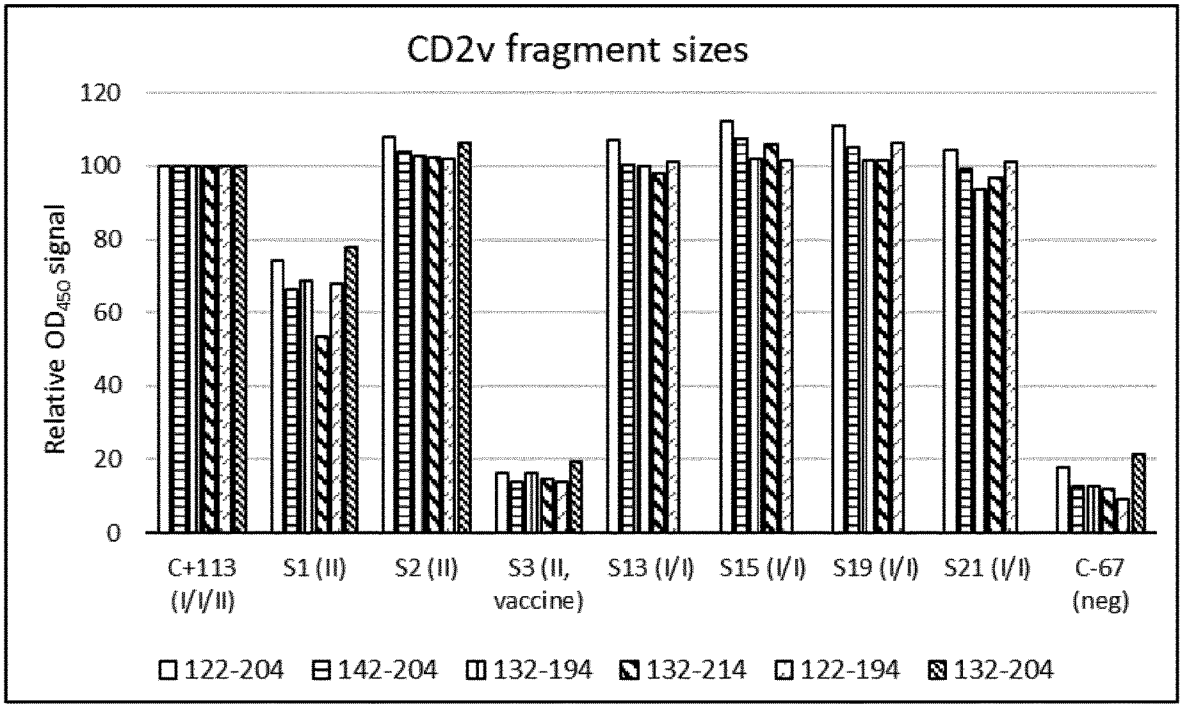

The results are presented in FIG. 7: for all peptides tested, sera from swine infected with genotype II ASFV strains (51 and S2), or genotype I ASFV strains (S13, S15, S19, S21), at a serum dilution of 1:300 showed a clear positive signal above the signal of the negative serum C-67. Serum sample C+113 gave also a clear positive signal that was set at 100%. As before, serum from an animal vaccinated with a genotype II strain (S3) did not react in the ELISA.

From this analysis it is clear that both the CD2v peptide fragments 132-194 (SEQ ID NO: 23) and 142-204 (SEQ ID NO: 24) provided a positive signal in the ELISA. Consequently, it is safe to conclude that the relevant epitope on that peptide is located between amino acids 142 and 194 of the CD2v protein. Therefore the peptide 142-194 (SEQ ID NO: 25) can effectively be used in the ASFV DIVA of the invention.

Example 6—Variations of the Sample Diluent

This Example tested the effect of variations in the composition of the sample diluent, on the signal-to-noise ratio of the ELISA for the invention.

A: Effect of Detergent Concentration in the Sample Diluent

CD2v fragment CD2 "132-204" was used, and the ELISA was performed as described in Example 1 with the exception that the test sera were diluted in different versions of a sample diluent: 0.01 M PBS+0.33% v/v Tween 20; 0.01 M PBS+3% v/v Tween 20; 0.01 M PBS+0.33% v/v Tween 80; 0.01 M PBS+3% v/v Tween 80: 0.01 M PBS; or into the LSHD buffer.

The CD2v-positive serum sample C+113 and the negative serum sample C-67 were included in the ELISA as well as serum sample S3 (derived from an animal infected with the Lv17/WB/Rie1 vaccine strain). For a reliable DIVA immunoassay, the $OD_{450}$ values for the S3 sample should be similar to that of the negative control serum.

Figure 8:
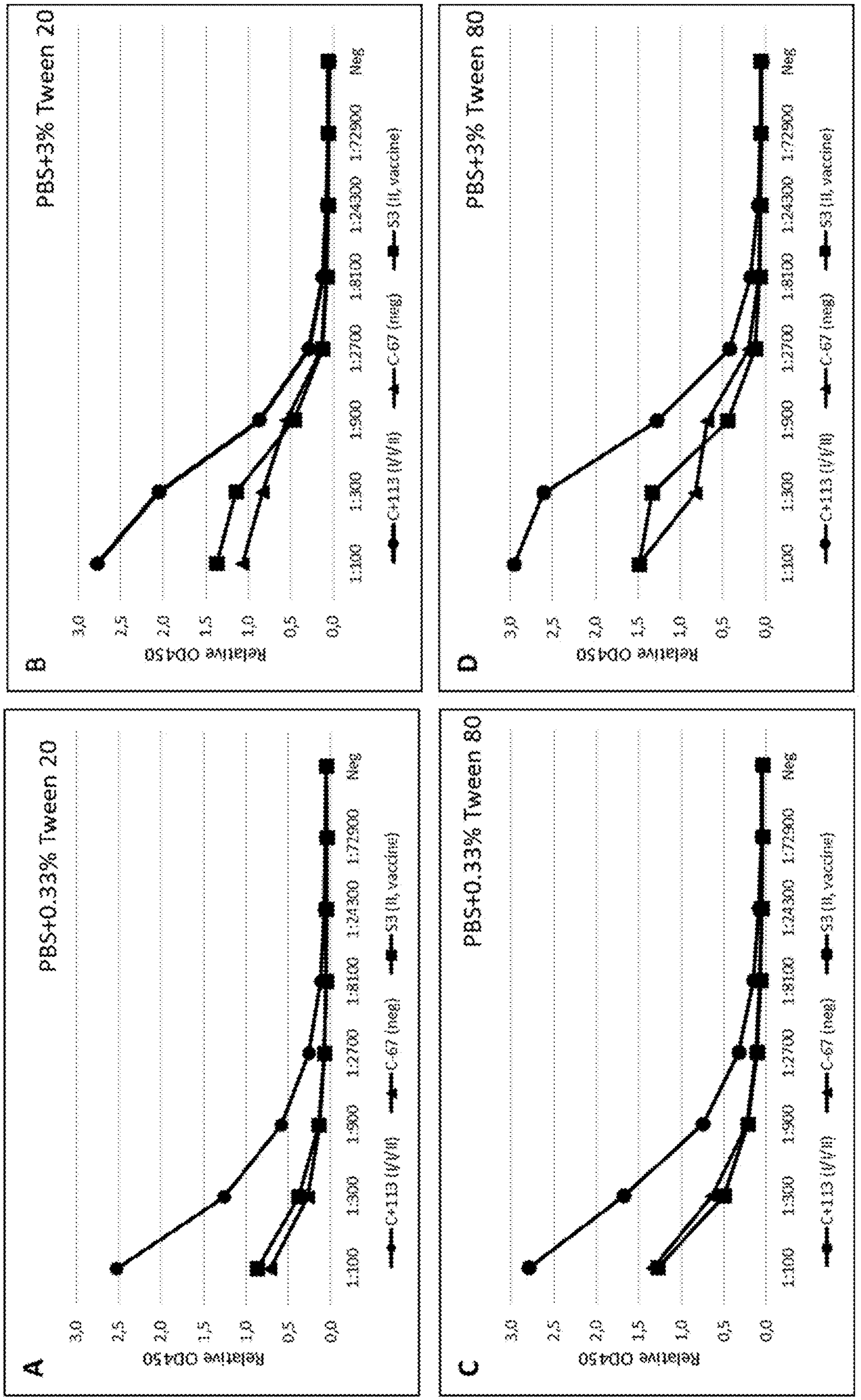
Figure 8:
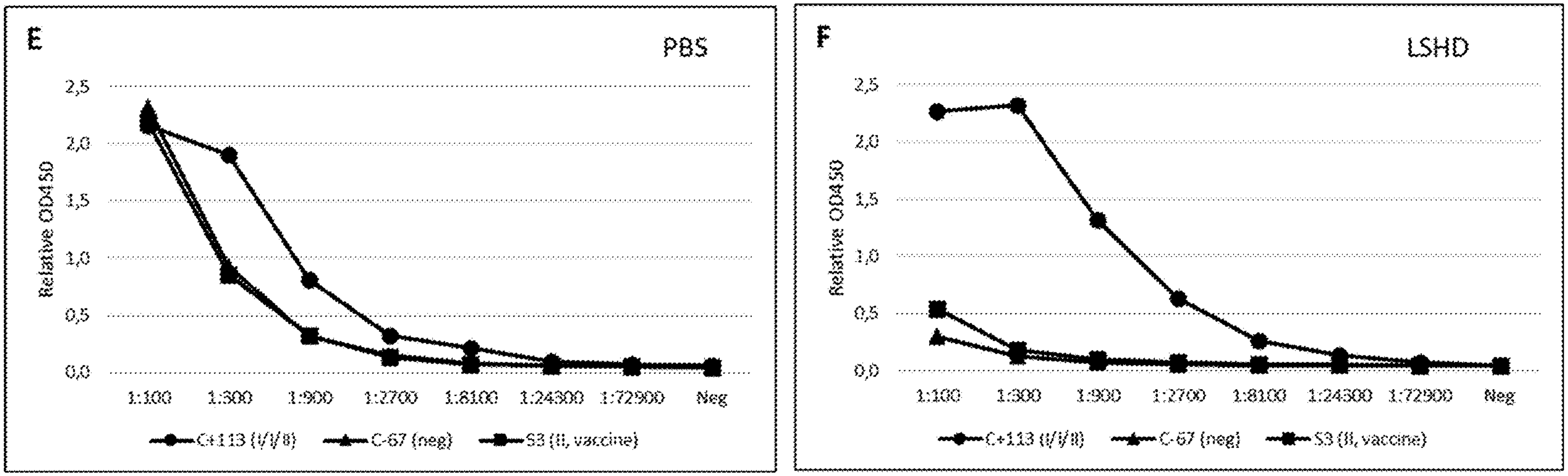

The ELISA results for the different sample diluents are presented in FIG. 8, and the corresponding P/N scores are presented in Table 3.

FIG. 8 panels A-E show that buffers containing Tween (panels 8 A-D) provided a better separation of the positive and negative samples than a diluent without Tween and only containing PBS (panel 8 E). This indicated that the presence of Tween in the sample diluent is important.

The corresponding P/N ratios as presented in Table 3 show that the LSHD buffer (panel 8 F) gave the best results, followed by the diluent with: 0.01 M PBS+0.33% v/v Tween 20. This also illustrates which sample diluents comply with having a stringency of 5 or more, or of 10 or more.

In general, buffers with Tween 20 provided better P/N ratios than buffers with Tween 80 instead.

TABLE 3

P/N ratios related to the data presented in FIG. 8

| Sample diluent | Positive/Negative ratios (for the dilutions) 1:100 | 1:300 | 1:900 | 1:2700 | 1:8100 | 1:24300 |
|---|---|---|---|---|---|---|
| 0.01M PBS + 0.33% v/v Tween 20 | 3.5 | 6.2 | 9.8 | 12.4 | 19.9 | 30.7 |
| 0.01M PBS + 3% v/v Tween 20 | 2.5 | 2.7 | 4.3 | 12.6 | 14.9 | 17.9 |
| 0.01M PBS + 0.33% v/v Tween 80 | 2.2 | 3.9 | 6.3 | 8.9 | 11.4 | 14.5 |
| 0.01M PBS + 3% Tween 80 | 2.1 | 2.6 | 3.2 | 7.1 | 12.3 | 17.1 |
| 0.01M PBS | 0.9 | 2.3 | 3.6 | 4.3 | 7.9 | 5.7 |
| LSHD | 5.4 | 16.5 | 25.4 | 27.7 | 43.6 | 40.3 |

B: Effect of Salt Concentration in the Sample Diluent

Again CD2v fragment CD2 "132-204" was used. The ELISA was performed as described in Example 1, but the sera were taken up in variations of the sample diluent: 0.01 M PBS+3% v/v Tween 20+0.1 M MgCl2; 0.01 M PBS+3% v/v Tween 20+0.33 M MgCl2; 0.01 M PBS+3% v/v Tween 20+1 M MgCl2; or into the LSHD buffer.

The CD2v-positive serum sample C+113 and the negative serum sample C-67 were included in the ELISA, as well as serum sample S3.

Figure 9:
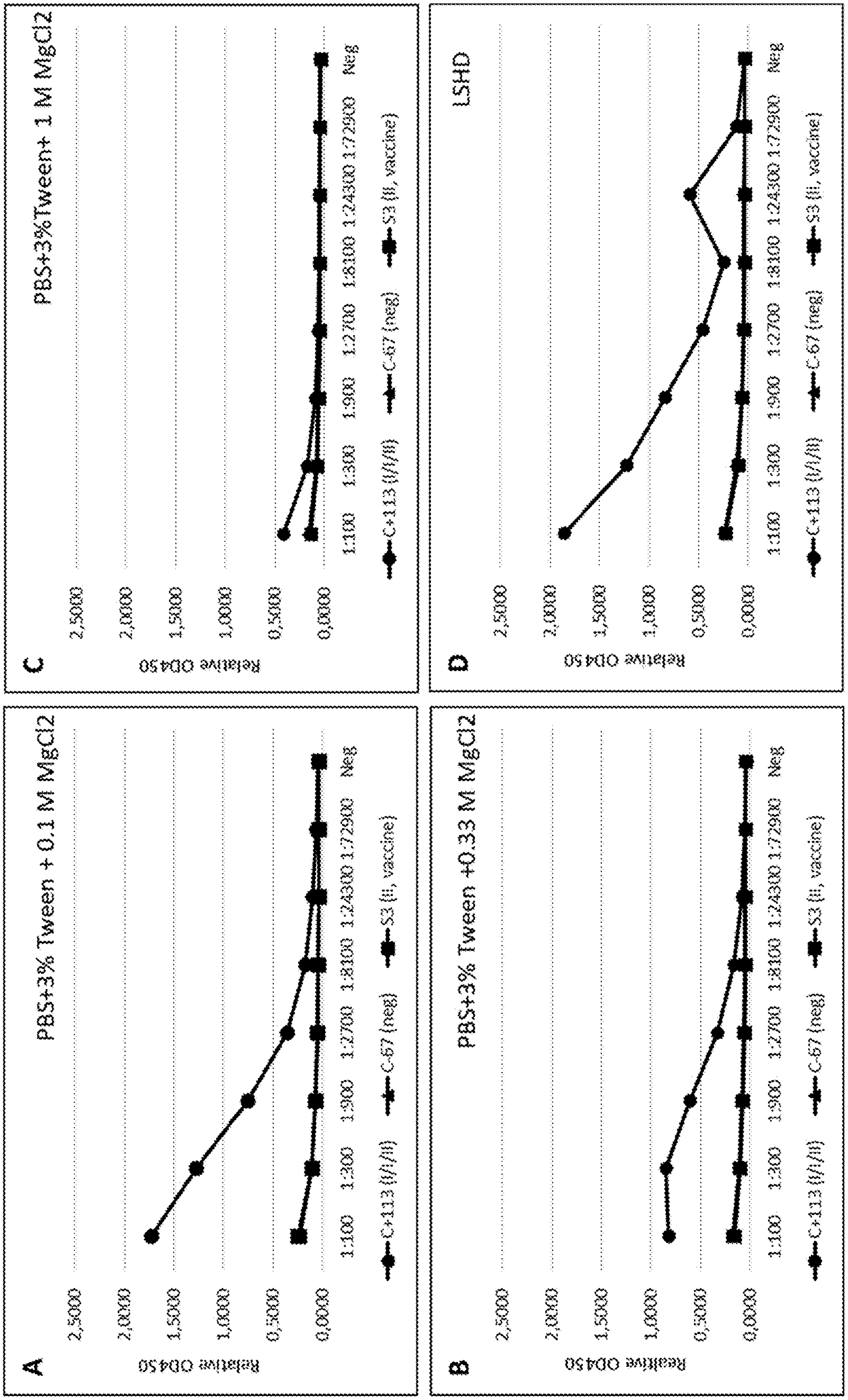

The ELISA results are presented in FIG. 9, and the corresponding P/N ratios in Table 4.

FIG. 9 panels A-C show that the lowest concentration of salt (i.e. 0.1 M MgCl2) in the sample diluent provided the best separation of the sample curves. In other words: by increasing the salt concentration, the capacity to distinguish between positive and negative samples is decreased (panels 9 B and C). Apparently, a lower salt concentration has a beneficial effect on the strength of the signal of the positive sample, which in turn has a positive effect on the P/N ration (Table 4).

LSHD as sample diluent provided the most optimal signal-to-noise ratio among the three diluents tested (FIG. 9 D; Table 4).

NB: In panel 9 D, the datapoint for the C+113 serum at dilution 1:24300 is clearly an outlier, and most likely an experimental fault.

TABLE 4

P/N ratios related to the data presented in FIG. 9

| Sample diluent | Positive/Negative ratios (for the dilutions) 1:100 | 1:300 | 1:900 | 1:2700 | 1:8100 | 1:24300 |
|---|---|---|---|---|---|---|
| 0.01M PBS + 3% v/v Tween 20 + 0.1M MgCl2 | 8.3 | 15.8 | 20.2 | 22.8 | 20.2 | 18.6 |
| 0.01M PBS + 3% v/v Tween 20 + 0.33M MgCl2 | 6.7 | 12.3 | 16.8 | 20.9 | 27.7 | 27.8 |
| 0.01M PBS + 3% v/v Tween 20 + 1.0M MgCl2 | 4.4 | 4.2 | 3.1 | 2.9 | 2.7 | 1.4 |
| LSHD | 8.5 | 16.6 | 33.8 | 38.8 | 50.9 | 74.0 |

C: Effect of a Buffer in the Sample Diluent

The CD2v fragment CD2 "132-204" was used. The ELISA was performed as described in Example 1, whereby the sera were taken up into sample diluent with: 0.01 M PBS+3% v/v Tween 20+0.1 M MgCl2; 3% v/v Tween 20+0.1 M MgCl2; 0.01 M PBS+3% v/v Tween 20; or into the LSHD diluent.

The CD2v-positive serum sample C+113 and the negative serum sample C-67 were included in the ELISA, as well as serum sample S3 which was derived from an animal inoculated with the Lv17/WB/Rie1 vaccine strain.

Figure 10:
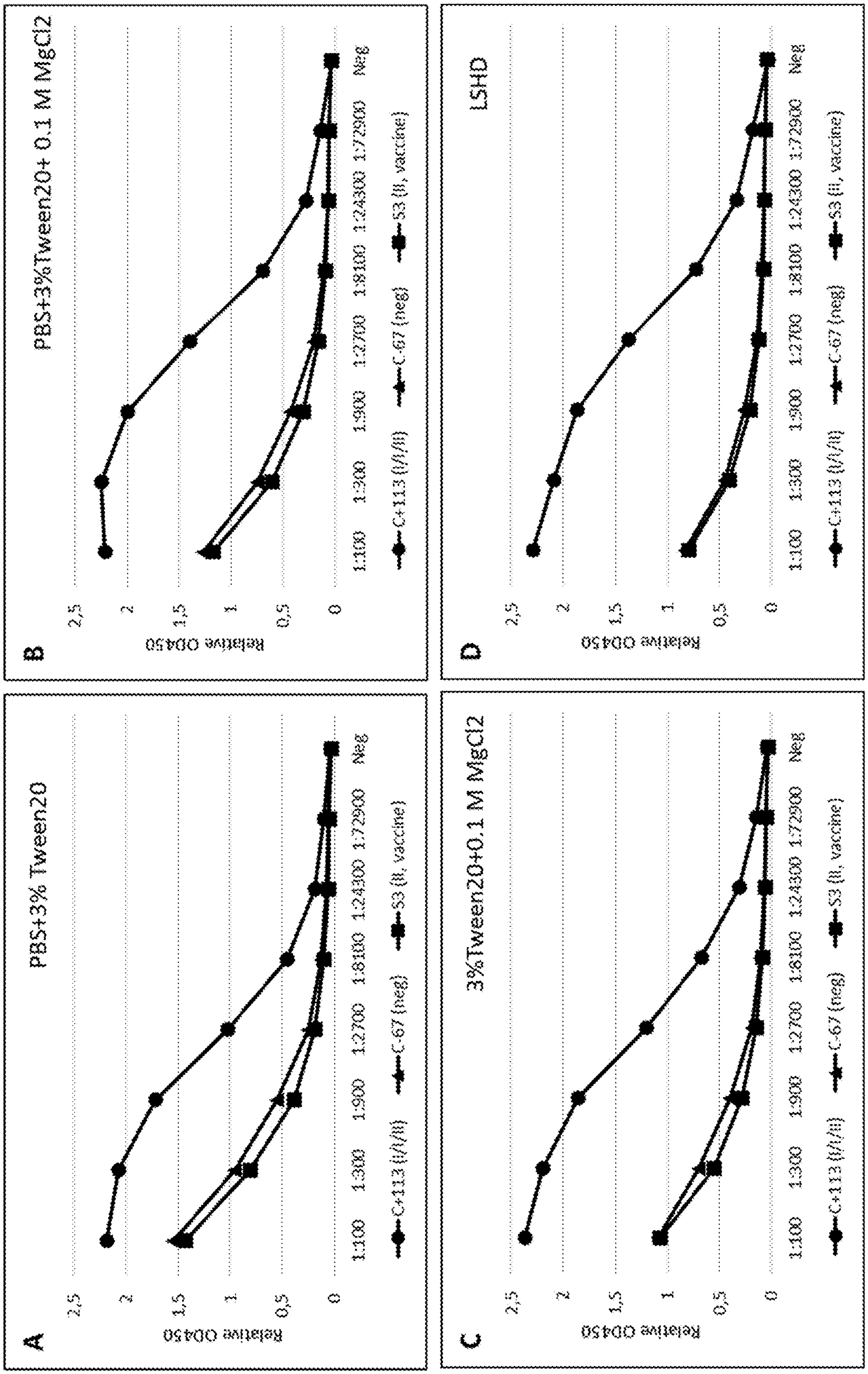

Results of the ELISA are presented in FIG. 10, and the corresponding P/N ratios are listed in Table 5.

FIG. 10 shows that all the buffers tested provided clear separation of the sample dilution curves. The sample diluent without PBS (having 3% v/v Tween 20+0.1 M MgCl2) performed almost as good as LSHD; compare panels 10 C and D, and the P/N ratios in Table 5. Therefore, it is preferable not to use PBS, or at least not to use a phosphate buffer, in the sample diluent for the invention.

TABLE 5

P/N ratios related to the data presented in FIG. 10

| Sample diluent | Positive/Negative ratios (for the dilutions) 1:100 | 1:300 | 1:900 | 1:2700 | 1:8100 | 1:24300 |
|---|---|---|---|---|---|---|
| PBS + 3% v/v Tween 20 | 1.6 | 2.5 | 4.2 | 6.8 | 8.4 | 7.6 |
| PBS + 3% v/v Tween 20 + 0.1M MgCl2 | 1.8 | 3.3 | 5.7 | 9.2 | 12.8 | 12.1 |
| 3% v/v Tween 20 + 0.1M MgCl2 | 2.2 | 3.6 | 6.1 | 10.3 | 16.0 | 16.7 |
| LSHD | 2.8 | 5.1 | 8.5 | 13.9 | 17.0 | 14.8 |

The invention claimed is:

1. A method for distinguishing if a swine is infected with a wild-type ASFV or vaccinated with an ASFV live attenuated virus CD2v-marker vaccine (LAV CD2v-marker vaccine), the method comprising the steps of:

adding a test sample obtained from the swine with an antigen, wherein the antigen is an isolated antigenic fragment of a ASFV CD2v protein and wherein the antigenic fragment is a polypeptide comprising an amino acid sequence with at least 95% amino acid sequence identity to SEQ ID NO: 25, incubating the sample with the antigen for a sufficient amount of time to allow the formation of an antibody-antigen complex, comprising an antibody from the test sample and the antigen, detecting the presence or absence of the antibody-antigen complex, and wherein the presence of the antibody-antigen complex identifies the swine from which the test sample is obtained as being infected with a wild-type ASFV, and the absence of an antibody-antigen complex identified the swine as vaccinated with a LAV CD2v-marker vaccine.

2. The method according to claim 1, wherein the antigenic fragment of the extracellular domain is a polypeptide comprising an ASFV amino acid sequence consisting of an amino acid sequence with at least 95% amino acid sequence identity to SEQ ID NO: 25.

3. The method according to claim 1, wherein the accompanying LAV CD2v-marker vaccine comprises an ASFV CD2v-marker vaccine strain that is capable of expressing an altered CD2v protein wherein the altered CD2v protein lacks a fragment of the extracellular domain comprising an amino acid sequence with at least 95% amino acid sequence identity to SEQ ID NO: 25.

4. The method according to claim 3, wherein the ASFV CD2v antigen has no epitope in common with the altered CD2v protein.

5. The method of Use according to claim 3, the ASFV CD2v antigen and the altered CD2v protein have no overlapping amino acid sequence.

6. The method according to claim 1, wherein the antigenic fragment is also used to detect the presence of ASFV antibodies in a test sample obtained from a swine infected with a wild-type ASFV and/or a swine uninfected with ASFV.

7. The method according to claim 1, wherein the antigenic fragment of a ASFV CD2v protein is immobilized to a solid support.

8. The method according to claim 7 wherein the solid support is a microtiter plate, vial, bead paper strip, membrane, gel or lateral flow strip.

9. The method according to claim 1, wherein the method comprises detecting the presence of the antibody-antigen complex by contacting the complex with an antibody comprising a label.

10. The method according to claim 8, wherein the antigen immobilized to a solid support is an immunoassay or is an ELISA (enzyme linked immunosorbent assay).

11. The method according to claim 1, wherein the test sample is diluted with a sample diluent having a stringency of at least 5.

12. The method according to claim 1, wherein the sample diluent has a stringency of at least 10.

13. The method of claim 1, wherein diluent does not contain phosphate buffer.

14. The method of claim 13, wherein the diluent is a low metal-salt, high detergent (LSHD) buffer that contains: 3% v/v Tween 20, 3% v/v Aminoxide WS 35, and 0.1 M magnesium-chloride.

* * * * *